United States Patent
Itagaki et al.

(10) Patent No.: US 11,141,363 B2
(45) Date of Patent: Oct. 12, 2021

(54) ULTRAVIOLET-SHIELDING PARTICLE COATED WITH SILICON OXIDE, AQUEOUS COMPOSITION CONTAINING ULTRAVIOLET-SHIELDING PARTICLE COATED WITH SILICON OXIDE, AND COSMETIC

(71) Applicant: SUMITOMO OSAKA CEMENT CO., LTD., Tokyo (JP)

(72) Inventors: Tetsuro Itagaki, Tokyo (JP); Hirokazu Matsushita, Tokyo (JP); Norito Morishita, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 0 days.

(21) Appl. No.: 16/476,109

(22) PCT Filed: Jan. 5, 2018

(86) PCT No.: PCT/JP2018/000065
§ 371 (c)(1),
(2) Date: Jul. 5, 2019

(87) PCT Pub. No.: WO2018/128189
PCT Pub. Date: Jul. 12, 2018

(65) Prior Publication Data
US 2019/0350822 A1   Nov. 21, 2019

(30) Foreign Application Priority Data

Jan. 6, 2017 (JP) .............................. JP2017-001082
Jan. 6, 2017 (JP) .............................. JP2017-001083

(51) Int. Cl.
*A61K 8/06* (2006.01)
*A61K 8/25* (2006.01)
*A61K 8/58* (2006.01)
*A61Q 17/04* (2006.01)
*A61K 8/27* (2006.01)
*A61K 8/28* (2006.01)

(52) U.S. Cl.
CPC .............. *A61K 8/062* (2013.01); *A61K 8/25* (2013.01); *A61K 8/27* (2013.01); *A61K 8/28* (2013.01); *A61K 8/585* (2013.01); *A61Q 17/04* (2013.01); *A61K 2800/412* (2013.01); *A61K 2800/622* (2013.01); *A61K 2800/651* (2013.01); *A61K 2800/82* (2013.01)

(58) Field of Classification Search
CPC . A61K 8/062; A61K 8/25; A61K 8/27; A61K 8/585; A61Q 17/04
See application file for complete search history.

(56) References Cited

U.S. PATENT DOCUMENTS

| | | | |
|---|---|---|---|
| 9,642,785 B2 | 5/2017 | Itagaki et al. | |
| 9,855,197 B2 | 1/2018 | Itagaki et al. | |
| 10,238,589 B2 * | 3/2019 | Itagaki | ............... A61K 8/0241 |
| 2012/0027709 A1 * | 2/2012 | Sato | ................... A61K 8/0241 424/69 |
| 2017/0266084 A1 | 9/2017 | Itagaki et al. | |

FOREIGN PATENT DOCUMENTS

| | | | |
|---|---|---|---|
| JP | 2002-160907 | * | 6/2002 |
| JP | 2013095797 | | 5/2013 |
| WO | 2014171322 | | 10/2014 |
| WO | 2015072499 | | 5/2015 |

OTHER PUBLICATIONS

ChEBI, methyl group, accessed Mar. 10, 2020, pp. 1-3 (Year: 2020).*
PubChem, Triethoxysilane, accessed Mar. 10, 2020, pp. 1-56 (Year: 2020).*
Sigma-Aldrich, Tetramethyl orthosilicate (accessed Jul. 16, 2020), pp. 1-4 (Year: 2020).*
Sigma-Adrich, Triethoxymethylsilane (acessed Dec. 23, 2020) pp. 3 (Year: 2020).*
"International Search Report (Form PCT/ISA/210) of PCT/JP2018/000065", dated Feb. 6, 2018, with English translation thereof, pp. 1-4.

* cited by examiner

*Primary Examiner* — Andrew S Rosenthal
*Assistant Examiner* — Lyndsey M Beckhardt
(74) *Attorney, Agent, or Firm* — JCIPRNET

(57) ABSTRACT

In an ultraviolet-shielding particle coated with silicon oxide of the present invention, a surface of the ultraviolet-shielding particle is coated with a silicon oxide coat, at least one functional group selected from the group consisting of an alkyl group, an alkenyl group, and a cycloalkyl group is present on a surface of the silicon oxide coat, and a content of the functional group is 0.0001% by mass or more and 0.30% by mass or less.

10 Claims, 4 Drawing Sheets

ULTRAVIOLET-SHIELDING PARTICLE COATED WITH SILICON OXIDE, AQUEOUS COMPOSITION CONTAINING ULTRAVIOLET-SHIELDING PARTICLE COATED WITH SILICON OXIDE, AND COSMETIC

CROSS-REFERENCE TO RELATED APPLICATION

This application is a 371 application of International PCT application serial no. PCT/JP2018/000065, filed on Jan. 5, 2018, which claims the priority benefit of Japan application no. 2017-001082, filed on Jan. 6, 2017, and Japan application no. 2017-001083, filed on Jan. 6, 2017. The entirety of each of the abovementioned patent applications is hereby incorporated by reference herein and made a part of this specification.

TECHNICAL FIELD

The present invention relates to an ultraviolet-shielding particle coated with silicon oxide, an aqueous composition containing an ultraviolet-shielding particle coated with silicon oxide, and a cosmetic.

Priority is claimed on Japanese Patent Application No. 2017-001082, filed on Jan. 6, 2017, and Japanese Patent Application No. 2017-001083, filed on Jan. 6, 2017, the contents of which are incorporated herein by reference.

BACKGROUND ART

Cosmetics containing ultraviolet-shielding particles are frequently used not only for leisure uses but also for daily uses. Therefore, for cosmetics, stress-free texture enabling daily use matters. In order to obtain such texture, aqueous cosmetics imparting fresh sensation are demanded as cosmetics.

Compared with oil-based cosmetics, aqueous cosmetics are less sticky and impose a smaller burden for skin and thus, in recent years, have been used as a variety of oil-in-water (O/W) cosmetics such as sunscreens, milk lotions, and creams.

As an ultraviolet-shielding particle available for the above-described aqueous cosmetics, a zinc oxide particle coated with silicon oxide is known (for example, refer to Patent Literature 1 and 2).

CITATION LIST

Patent Literature

[Patent Literature No. 1] International Publication No. WO2014/171322
[Patent Literature No. 2] International Publication No. WO2015/072499

SUMMARY OF INVENTION

Technical Problem

However, in the case of producing an aqueous cosmetic using the zinc oxide coated with silicon oxide described in Patent Literature 1 or Patent Literature 2, the zinc oxide coated with silicon oxide can be mixed into the aqueous cosmetic, but there has been a problem in that a desired ultraviolet-shielding property cannot be obtained in the case of forming a coated film.

The present invention has been made in consideration of the above-described circumstances, and an object of the present invention is to provide an ultraviolet-shielding particle coated with silicon oxide from which a desired ultraviolet-shielding property can be obtained even when applied to an aqueous cosmetic, an aqueous composition containing the ultraviolet-shielding particle coated with silicon oxide, and a cosmetic including the ultraviolet-shielding particle coated with silicon oxide and the aqueous composition.

Solution to Problem

As a result of repeating intensive studies in order to achieve the above-described object, the present inventors found that, in a case where an ultraviolet-shielding particle is coated with silicon oxide, and a predetermined functional group is caused to be present in a silicon oxide coat, thereby producing a coated film, it is possible to obtain an ultraviolet-shielding particle coated with silicon oxide from which a desired ultraviolet-shielding property can be obtained and completed the present invention.

A first aspect of the present invention is an ultraviolet-shielding particle coated with silicon oxide formed by coating a surface of the ultraviolet-shielding particle with a silicon oxide coat, in which at least one functional group selected from the group consisting of an alkyl group, an alkenyl group, and a cycloalkyl group is present on a surface of the silicon oxide coat, and a content of the functional group is 0.0001% by mass or more and 0.30% by mass or less.

A second aspect of the present invention is an aqueous composition containing an ultraviolet-shielding particle coated with silicon oxide containing the ultraviolet-shielding particle coated with silicon oxide and water.

A third aspect of the present invention is a cosmetic containing at least one of the ultraviolet-shielding particle coated with silicon oxide and the aqueous composition containing an ultraviolet-shielding particle coated with silicon oxide and a cosmetic product base raw material.

A fourth aspect of the present invention is an oil-in-water cosmetic formed by containing at least one of the ultraviolet-shielding particle coated with silicon oxide and the aqueous composition containing an ultraviolet-shielding particle coated with silicon oxide in a water phase.

Advantageous Effects of Invention

According to the ultraviolet-shielding particle coated with silicon oxide of the present invention, the ultraviolet-shielding particle coated with silicon oxide is excellent in terms of an ultraviolet-shielding property even when applied to an aqueous cosmetic.

According to the aqueous composition containing an ultraviolet-shielding particle coated with silicon oxide of the present invention, the aqueous composition containing an ultraviolet-shielding particle coated with silicon oxide contains the ultraviolet-shielding particle coated with silicon oxide of the present invention and is thus excellent in terms of an ultraviolet-shielding property even when applied to an aqueous cosmetic.

According to the cosmetic of the present invention, the cosmetic contains at least one of the ultraviolet-shielding particle coated with silicon oxide of the present invention and the aqueous composition containing an ultraviolet-shielding particle coated with silicon oxide of the present invention and is thus excellent in terms of an ultraviolet-shielding property.

According to the oil-in-water cosmetic of the present invention, the oil-in-water cosmetic contains at least one of the ultraviolet-shielding particle coated with silicon oxide of the present invention and the aqueous composition containing an ultraviolet-shielding particle coated with silicon oxide of the present invention and is thus excellent in terms of an ultraviolet-shielding property.

DESCRIPTION OF EMBODIMENTS

Figure 1:
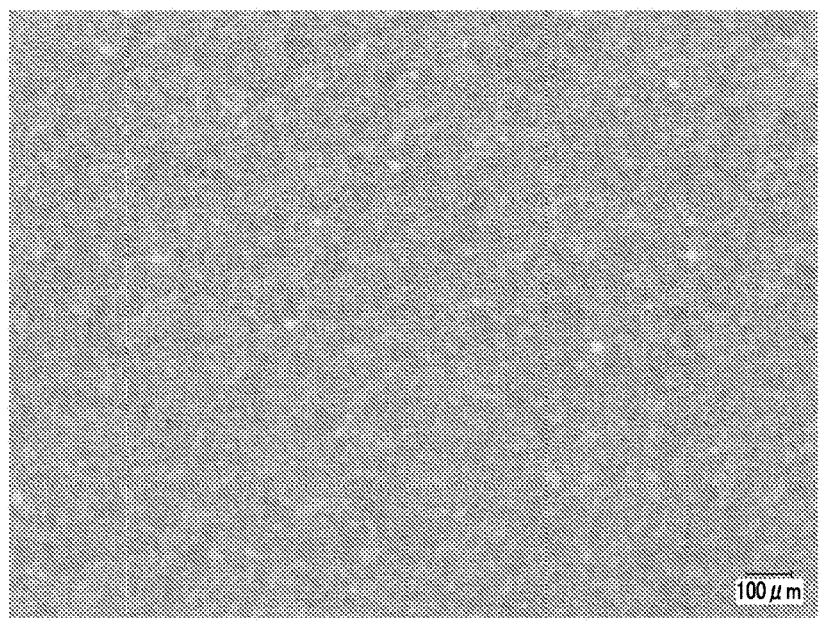
FIG. 1 is a view showing an optical microscopic image of an aqueous composition containing zircon oxide particles coated with silicon oxide of Example 1.

Preferred aspects for carrying out an ultraviolet-shielding particle coated with silicon oxide, an aqueous composition containing an ultraviolet-shielding particle coated with silicon oxide, a cosmetic containing the ultraviolet-shielding particle coated with silicon oxide and the aqueous composition containing an ultraviolet-shielding particle coated with silicon oxide, and an oil-in-water cosmetic of the present invention will be described.

The following embodiment is specific description for better understanding the gist of the present invention and, unless particularly otherwise described, does not limit the present invention.

[Ultraviolet-Shielding Particle Coated with Silicon Oxide]

An ultraviolet-shielding particle coated with silicon oxide of the present embodiment is formed by coating a surface of the ultraviolet-shielding particle with a silicon oxide coat, at least one functional group selected from the group consisting of an alkyl group, an alkenyl group, and a cycloalkyl group is present on a surface of the silicon oxide coat, and the content of the functional group is 0.0001% by mass or more and 0.30% by mass or less.

In detail, the ultraviolet-shielding particle coated with silicon oxide of the present embodiment has an ultraviolet-shielding particle and a silicon oxide coat that coats the surface of the ultraviolet-shielding particle, and a thin film made of a silica (silicon oxide ($SiO_2$)) compound having at least one functional group selected from the group consisting of an alkyl group, an alkenyl group, and a cycloalkyl group is present on the surface (outermost surface) of the silicon oxide coat. That is, in the ultraviolet-shielding particle coated with silicon oxide of the present embodiment, the silicon oxide coat includes silicon and the above-described functional group (in detail, the compound having the above-described functional group). Therefore, in the ultraviolet-shielding particle coated with silicon oxide of the present embodiment, at least one functional group selected from the group consisting of an alkyl group, an alkenyl group, and a cycloalkyl group is present on the surface of the silicon oxide coat. In addition, the silica compound having the functional group refers to a compound in which the surface of silica is surface-treated with an organic silicon compound or the like described below. That is, the silica compound having the functional group refers to a compound having at least one functional group selected from the group consisting of an alkyl group, an alkenyl group, and a cycloalkyl group derived from an organic silicon compound or the like on the surface of silica.

At least one functional group selected from the group consisting of an alkyl group, an alkenyl group, and a cycloalkyl group is present is not particularly limited as long as compatibility with an oil component can be improved.

In the alkyl group, the number of carbon atoms is preferably 1 or more and 8 or less, more preferably 1 or more and 6 or less, still more preferably 1 or more and 4 or less, and most preferably 1 or more and 2 or less.

When the number of carbon atoms in the alkyl group is 1 or more and 8 or less, the hydrophilicity of the silicon oxide coat is not excessively impaired, and the excessive presence of at least one functional group selected from the group consisting of an alkyl group, an alkenyl group, and a cycloalkyl group is present on the surface of the silicon oxide coat can be suppressed. Therefore, in the case of using the ultraviolet-shielding particle coated with silicon oxide of the present embodiment in an aqueous cosmetic or an oil-in-water cosmetic, a desired ultraviolet-shielding property can be obtained.

In the ultraviolet-shielding particle coated with silicon oxide of the present embodiment, the content of at least one selected from the group consisting of an alkyl group, an alkenyl group, and a cycloalkyl group is 0.0001% by mass or more and 0.30% by mass or less, preferably 0.01% by mass or more and 0.25% by mass or less, more preferably 0.02% by mass or more and 0.20% by mass or less, and still more preferably 0.02% by mass or more and 0.10% by mass or less of the total amount (100% by mass) of the ultraviolet-shielding particle coated with silicon oxide. In a case where two or more functional groups are contained, the total content of these functional groups is preferably in the above-described range.

When the content of at least one functional group selected from the group consisting of an alkyl group, an alkenyl group, and a cycloalkyl group is in the above-described range, the hydrophilicity of the silicon oxide coat is not excessively impaired, and the excessive presence of at least one functional group selected from the group consisting of an alkyl group, an alkenyl group, and a cycloalkyl group is present on the surface of the silicon oxide coat can be suppressed. Therefore, in the case of using the ultraviolet-shielding particle coated with silicon oxide of the present embodiment in an aqueous cosmetic or an oil-in-water cosmetic, a desired ultraviolet-shielding property can be obtained.

In the ultraviolet-shielding particle coated with silicon oxide of the present embodiment, the content of the ultraviolet-shielding particle is preferably 50% by mass or more and 95% by mass or less, more preferably 60% by mass or more and 90% by mass or less, and still more preferably 70% by mass or more and 80% by mass or less of the total amount (100% by mass) of the ultraviolet-shielding particle coated with silicon oxide.

When the content of the ultraviolet-shielding particle is in the above-described range, in the case of using the ultraviolet-shielding particle coated with silicon oxide of the present embodiment in an aqueous cosmetic or an oil-in-water cosmetic, a desired ultraviolet-shielding property can be obtained. In addition, it is possible to mix the ultraviolet-shielding particle coated with silicon oxide of the present embodiment into an aqueous cosmetic or an oil-in-water cosmetic.

In the ultraviolet-shielding particle coated with silicon oxide of the present embodiment, the content of the silicon oxide is preferably 3% by mass or more and 45% by mass or less, more preferably 10% by mass or more and 40% by mass or less, and still more preferably 15% by mass or more and 35% by mass or less of the total amount (100% by mass) of the ultraviolet-shielding particle coated with silicon oxide. From the viewpoint of suppressing the elution of a metal ion in the ultraviolet-shielding particle, the content of the silicon oxide is preferably 15% by mass or less. From the viewpoint of obtaining a desired ultraviolet-shielding property, the content of the silicon oxide is preferably 30% by mass or less. In a case where the average primary particle diameter of the ultraviolet-shielding particles is 50 nm or less, the content of the silicon oxide is preferably 3% by mass or more and 45% by mass or less. In addition, in a case where the average primary particle diameter of the ultraviolet-shielding particles is more than 50 nm, the content of the silicon oxide is preferably 1% by mass or more and 35% by mass or less.

The ultraviolet-shielding particle is not particularly limited as long as the ultraviolet-shielding particle is a metal oxide particle capable of shielding ultraviolet rays. As such an ultraviolet-shielding particle, for example, at least one selected from the group consisting of a zinc oxide particle, a titanium oxide particle, and a cerium oxide particle is exemplified. Among these, a zinc oxide particle and a titanium oxide particle are preferred since those particles are generally used as an ultraviolet-shielding particle for cosmetics.

In the ultraviolet-shielding particle coated with silicon oxide of the present embodiment, when an abundance ratio of silicon in the silicon oxide coat in a $Q^3$ environment is represented by $Q^3$, and an abundance ratio of silicon in the silicon oxide coat in a $Q^4$ environment is represented by $Q^4$, $Q^3+Q^4 \geq 0.6$ and $Q^4/(Q^3+Q^4) \geq 0.5$ are preferred. Furthermore, the entire ultraviolet-shielding particle coated with silicon oxide is preferably uniformly coated with the silicon oxide coat so that the decomposition rate of Brilliant Blue that is generated by the photocatalytic activity of the ultraviolet-shielding particle coated with silicon oxide reaches 3% or lower. The decomposition rate of Brilliant Blue that is generated by the photocatalytic activity of the ultraviolet-shielding particle coated with silicon oxide more preferably reaches 2% or lower and still more preferably 1% or lower.

The silicon oxide coat needs to have a high degree of condensation so that "when the abundance ratio of silicon in the silicon oxide coat in the $Q^3$ environment is represented by $Q^3$, and the abundance ratio of silicon in the silicon oxide coat in the $Q^4$ environment is represented by $Q^4$, $Q^3+Q^4 \geq 0.6$ and $Q^4/(Q^3+Q^4) \geq 0.5$" are satisfied.

There is a close relationship between the "denseness" of the silicon oxide coat and the "degree of condensation" of silicon oxide, and the denseness of the silicon oxide coat increases as the degree of condensation of silicon oxide increases.

That is, the "denseness" of a dense silicon oxide coat mentioned herein refers to the silicon oxide coat in a state in which the degree of condensation of silicon oxide is so high that $Q^3+Q^4 \geq 0.6$ and $Q^4/(Q^3+Q^4) \geq 0.5$" are satisfied.

When the silicon oxide coat is dense, it is possible to suppress the elution of the metal ion in the ultraviolet-shielding particle from the ultraviolet-shielding particle coated with silicon oxide of the present embodiment.

The degree of condensation of silicon oxide can be readily learned by measuring the NMR spectrum of the ultraviolet-shielding particle coated with silicon oxide by solid[29] Si MAS-nuclear magnetic resonance (NMR) spectrometry and measuring the area ratios of signals belonging to the respective environments of $Q^0$, $Q^1$, $Q^2$, $Q^3$, and $Q^4$ from the peak area ratio of this NMR spectrum.

Here, $Q^n$ (n=0 to 4) represents a chemical structure that is determined according to the number of crosslinking oxygen atoms among oxygen atoms in a $SiO_4$ tetrahedron unit that is a configurational unit of silicon oxide, that is, oxygen atoms bonding to two Si's.

The area ratios of the signals belonging to the respective environments of $Q^0$, $Q^1$, $Q^2$, $Q^3$, and $Q^4$ will be expressed as $Q^0$, $Q^1$, $Q^2$, $Q^3$, and $Q^4$. Here, $Q^0+Q^1+Q^2+Q^3+Q^4=1$.

The reason that the decomposition rate of Brilliant Blue that is generated by the photocatalytic activity of the ultraviolet-shielding particle coated with silicon oxide is preferably 3% or lower will be described below. The reason is that, when the decomposition rate of Brilliant Blue is 3% or lower, the photocatalytic activity of the ultraviolet-shielding particle is suppressed, and thus the homogeneity of the silicon oxide coat that covers the ultraviolet-shielding particle is also high. Here, the expression "the homogeneity of the silicon oxide coat that covers the ultraviolet-shielding particle being high" indicates that there is no coating unevenness, the coat is not localized, and there is no pin hole, or the like. The decomposition rate of Brilliant Blue is used as an index of the photocatalytic activity of the ultraviolet-shielding particle. The photocatalytic reaction of the ultraviolet-shielding particle basically occurs on the surface of the ultraviolet-shielding particle. That is, the fact that the decomposition rate of Brilliant Blue that is generated by the photocatalytic activity of the ultraviolet-shielding particle is low indicates that the number of places in which the ultraviolet-shielding particle is exposed is small on the surface of the ultraviolet-shielding particle coated with silicon oxide is small.

A method for measuring the decomposition rate of Brilliant Blue is as described below.

First, a Brilliant Blue aqueous solution containing a predetermined content (for example, 5 ppm) of Brilliant Blue is prepared, a predetermined amount is extracted from the Brilliant Blue aqueous solution to a screw pipe, the ultraviolet-shielding particle coated with silicon oxide is injected into the extracted Brilliant Blue aqueous solution in an amount of 1% by mass of the mass of the aqueous solution in terms of the ultraviolet-shielding particle and is ultrasonic-dispersed, thereby preparing a suspension.

Next, ultraviolet rays having a predetermined wavelength are radiated to the suspension using an ultraviolet radiation lamp from a predetermined distance (for example, 10 cm) for a predetermined time (for example, six hours). As the ultraviolet radiation lamp, for example, a bactericidal lamp GL20 (wavelength: 253.7 nm, ultraviolet output: 7.5 W, manufactured by Toshiba Corporation) can be used.

Next, a supernatant liquid is extracted from the suspension irradiated with ultraviolet rays, and the respective absorption photometric spectra of the Brilliant Blue aqueous solution and the supernatant liquid are measured by atomic absorption photometry.

In addition, a decomposition rate D of Brilliant Blue is calculated from Expression (1) using these measurement values.

$$D=(A0-A1)/A0 \quad (1)$$

(Here, A0 represents the absorbance at the absorption maximum wavelength (630 nm) of the absorption photometric spectrum of Brilliant Blue (5 ppm), and A1 represents the absorbance at the absorption maximum wavelength of the absorption photometric spectrum of the supernatant liquid)

The decomposition rate of Brilliant Blue of a zinc oxide particle (average particle diameter: 35 nm, manufactured by Sumitomo Osaka Cement Co., Ltd.) that is an ordinary ultraviolet-shielding particle is measured on the basis of the above-described method and is found out to be 90%. From this fact, it was confirmed that, when the zinc oxide particle (average particle diameter: 35 nm, manufactured by Sumitomo Osaka Cement Co., Ltd.) has a photocatalytic activity, the decomposition rate of Brilliant Blue is high.

The average primary particle diameter of the ultraviolet-shielding particles coated with silicon oxide is preferably 1 nm or larger and 2 μm or smaller and is appropriately adjusted in the above-described range in order to obtain desired transparency and a desired ultraviolet-shielding property of the ultraviolet-shielding particle coated with silicon oxide. In a case where it is necessary to improve transparency at the time of applying a cosmetic such as a sunscreen into which the ultraviolet-shielding particle coated with silicon oxide of the present embodiment is blended, the average primary particle diameter of the ultraviolet-shielding particles coated with silicon oxide is preferably 1 nm or larger and 50 nm or smaller. In a case where it is necessary to improve an ultraviolet-shielding property, the average primary particle diameter of the ultraviolet-shielding particles coated with silicon oxide is preferably 50 nm or larger and 2 μm or smaller.

The "average primary particle diameter" in the ultraviolet-shielding particle coated with silicon oxide of the present embodiment refers to a numerical value obtained using the following method. That is, in the case of observing the ultraviolet-shielding particle coated with silicon oxide of the present embodiment using a transmission electron microscope (TEM) or the like, a predetermined number of the ultraviolet-shielding particles, for example, 200 particles or 100 particles are selected. In addition, the longest linear portions (maximum long diameters) of the respective ultraviolet-shielding particles coated with silicon oxide are measured, and the weighted average of these measurement values is obtained.

In a case where the ultraviolet-shielding particles coated with silicon oxide agglomerate together, the agglomerated particle diameter of the agglomerate is not measured. Instead, a predetermined number of the ultraviolet-shielding particles coated with silicon oxide (primary particles) that configure the agglomerate are measured, and the average primary particle diameter is obtained.

When the ultraviolet-shielding particle coated with silicon oxide of the present embodiment is immersed in an aqueous solution having a hydrogen-ion exponent of five for one hour so that the content thereof reaches 0.05% by mass, the elution rate of the metal ion in the ultraviolet-shielding particle that is eluted into the aqueous solution is preferably 60% by mass or less, more preferably 20% by mass or less, and still more preferably 10% by mass or less.

Here, the reason that the elution rate of the metal ion is preferably 60% by mass or less is that, when the elution rate of the metal ion exceeds 60% by mass, the stability of the ultraviolet-shielding particle coated with silicon oxide degrades, and, in the case of applying the ultraviolet-shielding particle coated with silicon oxide to a cosmetic, the metal ion being eluted reacts with a water-soluble polymer such as an organic ultraviolet-shielding agent or a viscosity improver or the like, and the degradation of performance as the cosmetic, discoloration, a change in the viscosity, and the like are caused, which is not preferable.

The elution rate of the metal ion can be obtained by, for example, dispersing the ultraviolet-shielding particles coated with silicon oxide in a buffer solution having a pH of five so that the content thereof reaches 0.05% by mass, stirring the particles for one hour, then, separating solid and liquid, and measuring the concentration of metal in a liquid phase using an ICP emission analysis device.

The buffer solution having a pH of five is not particularly limited as long as the buffer solution is capable of dispersing the ultraviolet-shielding particles coated with silicon oxide, and, for example, a buffer solution obtained by mixing 500 mL of a 0.1 mol/L potassium hydrogen phthalate aqueous solution and 226 mL of a 0.1 mol/L sodium hydroxide aqueous solution and then adding water thereto so that the total amount reaches 1,000 mL is preferably used.

The average primary particle diameter of the ultraviolet-shielding particles is appropriately adjusted depending on desired transparency and a desired ultraviolet-shielding property. In a case where it is necessary to improve the transparency, the average primary particle diameter of the ultraviolet-shielding particles is preferably 1 nm or larger and 50 nm or smaller. In a case where it is necessary to improve the ultraviolet-shielding property, the average primary particle diameter of the ultraviolet-shielding particles is preferably 50 nm or larger and 500 nm or smaller. In a case where it is necessary to improve the transparency and the ultraviolet-shielding property, the average primary particle diameter of the ultraviolet-shielding particles is preferably 25 nm or larger and 250 nm or smaller.

A method for producing the ultraviolet-shielding particle coated with silicon oxide having the above-described dense silicon oxide coat is described in detail in International Publication No. WO2014/171322. According to this production method, a zinc oxide particle, the ultraviolet-shielding particle coated with silicon oxide having the dense silicon oxide coat can be obtained by coating the surface of an ultraviolet-shielding particle using alkoxysilane or sodium silicate and alkoxysilane and calcinating the ultraviolet-shielding particle at 200° C. to 600° C.

In the case of using ultraviolet-shielding particles having an average primary particle diameter of 50 nm or larger, the ultraviolet-shielding particles may be calcinated at 150° C. to 600° C.

In addition, the silicon oxide coat of the present embodiment preferably contains at least one selected from the group consisting of Mg, Ca, and Ba. The reason therefor is as described below.

In order to uniformly coat the entire surface of the ultraviolet-shielding particle with the silicon oxide coat so that the decomposition rate of Brilliant Blue that is generated by the photocatalytic activity of the ultraviolet-shielding particle coated with silicon oxide reaches 3% or lower, the silicon oxide coat is preferably formed using a material including an alkali metal such as sodium silicate. However, when this alkali metal remains in the ultraviolet-shielding particle coated with silicon oxide, an alkali ion is eluted at the time of mixing the ultraviolet-shielding particle coated with silicon oxide with water, the pH or viscosity significantly changes, and the quality stability as a cosmetic is impaired.

Therefore, the alkali metal that is included in the silicon oxide coat of the ultraviolet-shielding particle coated with silicon oxide is removed from the silicon oxide coat of the ultraviolet-shielding particle coated with silicon oxide by substituting the alkali metal that is included in the silicon oxide coat of the ultraviolet-shielding particle coated with silicon oxide with at least one selected from the group consisting of Mg, Ca, and Ba.

At least one selected from the group consisting of Mg, Ca, and Ba that substitutes the alkali metal that is included in the silicon oxide coat is present in the silicon oxide coat of the ultraviolet-shielding particle coated with silicon oxide after the substitution. Mg, Ca, and Ba that substitute the alkali metal are present as magnesium silicate, calcium silicate, barium silicate, or the like which has a low solubility in water.

As a result of the substitution, the total mass percentage of at least one selected from the group consisting of Mg, Ca, and Ba that is included in the silicon oxide coat of the ultraviolet-shielding particle coated with silicon oxide becomes larger than the mass percentage of the alkali metal that is included in the silicon oxide coat. Therefore, even when the ultraviolet-shielding particle coated with silicon oxide is mixed into a water phase, the elution of the alkali metal is suppressed, a change in the pH or viscosity can be suppressed, and it is possible to maintain the quality stability as a cosmetic.

The ultraviolet-shielding particle coated with silicon oxide of the present embodiment preferably contains at least one selected from the group consisting of Mg, Ca, and Ba.

The total mass percentage of at least one selected from the group consisting of Mg, Ca, and Ba that is included in the silicon oxide coat in the ultraviolet-shielding particle coated with silicon oxide is preferably larger than the mass percentage of the alkali metal that is included in the silicon oxide coat. Furthermore, the ratio of the mass percentage of the alkali metal that is included in the silicon oxide coat to the total mass percentage of at least one selected from the group consisting of Mg, Ca, and Ba that is included in the silicon oxide coat (the mass percentage of the alkali metal/ the total mass percentage of at least one selected from the group consisting of Mg, Ca, and Ba) is preferably 0.001 or higher and 0.6 or lower, more preferably 0.01 or higher and 0.5 or lower, and still more preferably 0.1 or higher and 0.4 or lower.

In the present embodiment, the alkali metal refers to an ordinarily-known alkali metal and is specifically at least one selected from the group consisting of lithium (Li), sodium (Na), potassium (K), rubidium (Rb), cesium (Cs), and francium (Fr).

Here, the reason for setting the total mass percentage of at least one selected from the group consisting of Mg, Ca, and Ba that is included in the silicon oxide coat to be larger than the mass percentage of the alkali metal that is included in the silicon oxide coat is that a cause for the change in the hydrogen-ion exponent (pH) of the ultraviolet-shielding particle coated with silicon oxide in the initial phase is not the metal ion that is eluted from the ultraviolet-shielding particle but the elution of the alkali metal ion that is included in the silicon oxide coat.

The mass percentage of the alkali metal that is included in the silicon oxide coat in the ultraviolet-shielding particle coated with silicon oxide is preferably 0.8% by mass or less, more preferably 0.6% by mass or less, and still more preferably 0.2% by mass or less.

The lower limit value of the mass percentage of the alkali metal that is included in the silicon oxide coat can be arbitrarily selected. The mass percentage of the alkali metal may be 0% by mass, and, as other examples, for example, 0.0001% by mass or more, 0.001% by mass or more, and the like can be exemplified.

The total mass percentage of at least one selected from the group consisting of Mg, Ca, and Ba that is included in the silicon oxide coat in the ultraviolet-shielding particle coated with silicon oxide is preferably 0.01% by mass or more and 1% by mass or less.

The mass percentage (mass %) of the alkali metal, Mg, Ca, and Ba that are included in the ultraviolet-shielding particle coated with silicon oxide (the silicon oxide coat) can be measured by atomic absorption photometry.

Regarding the ultraviolet-shielding particle coated with silicon oxide of the present embodiment, the spectral transmittance at 360 nm of an oil phase of a liquid mixture that is prepared by mixing a composition made up of 46.0 parts by mass of a gel obtained by mixing water and 0.2 parts by mass of an alkyl-modified carboxy vinyl polymer and adjusting the pH to 6.0 using 2.5 mol/L of sodium hydroxide, 50 parts by mass of the ultraviolet-shielding particle coated with silicon oxide, and 4.0 parts by mass of glycerin and decamethylcyclopentasiloxane in a mass ratio of 1:1 and dispersing the liquid mixture with ultrasonic waves for 10 minutes and is left to stand for 20 hours is preferably 100%, and the particle diameter of an agglomerate that is observed when 10 parts by mass of the composition and 90 parts by mass of a carboxy vinyl polymer are mixed together, and the mixture is sandwiched between glass slides and observed using an optical microscope is preferably 50 µm or smaller.

The carboxy vinyl polymer gel refers to an aqueous solution containing 1.5% by mass of a carbomer (trade name: Carbopol Ultrez 10 polymer, manufactured by Lubrizol Advanced Materials) and having a pH of 7.5 prepared by dissolving 1.5 g of the carbomer in pure water and then adding a 10% by mass sodium hydroxide aqueous solution dropwise.

As the alkyl-modified carboxy vinyl polymer, the following polymers are exemplified.

Decamethylcyclopentasiloxane is one of cyclic siloxanes, and the cyclic siloxanes area collective term of cyclic organic compounds. As the cyclic siloxanes, for example, hexamethylcyclotrisiloxane, octamethylcyclotetrasiloxane, decamethylcyclopentasiloxane, and the like are exemplified. Decamethylcyclopentasiloxane is used in cosmetics.

As the spectral transmittance (diffusion transmittance) at 360 nm of the oil phase of the liquid mixture, a value of the transmittance at 360 nm of the oil phase collected from the liquid mixture that is measured using a silica cell having an optical path length of 1 cm and an SPF analyzer UV-1000S (manufactured by Labsphere) was used.

When the spectral transmittance at 360 nm of the oil phase of the liquid mixture is less than 100%, the ultraviolet-shielding particles coated with silicon oxide are partially dispersed not only in the water phase but also in the oil phase, partially migrate from the water phase to the oil phase over time in the case of blending the ultraviolet-shielding particles coated with silicon oxide into the water phase of the cosmetic, and impair the stability of the formulation in some cases, which is not preferable.

As the particle diameter of an agglomerate that is observed at the time of observing the mixture sandwiched between glass slides using an optical microscope, the long diameter of the maximum agglomerate in three 13.5 µm×18 µm views obtained using the optical microscope at a magnification of 200 times was measured.

The reason for mixing the composition and the carboxy vinyl polymer gel in the case of measuring the particle diameter of the agglomerate is that, when the agglomerate is generated at the time of mixing the composition made up of 46.0 parts by mass of the gel obtained by mixing water and 0.2 parts by mass of an alkyl-modified carboxy vinyl polymer and adjusting the pH to 6.0 using 2.5 mol/L of sodium hydroxide, 50 parts by mass of the ultraviolet-shielding particle coated with silicon oxide, and 4.0 parts by mass of glycerin and the carboxy vinyl polymer gel, the agglomerate is generated at the time of blending the ultraviolet-shielding particle coated with silicon oxide into an aqueous composition, and a desired sun protection factor (SPF) cannot be obtained.

As the carboxy vinyl polymer that is used in the carboxy vinyl polymer gel, the following polymers are exemplified.

The maximum particle diameter of the agglomerate that is observed at the time of observing the mixture sandwiched between glass slides using an optical microscope exceeding 50 µm indicates that the ultraviolet-shielding particles coated with silicon oxide are likely to be agglomerated in the aqueous composition. In a case where the ultraviolet-shielding particle coated with silicon oxide is blended into the aqueous composition, it becomes difficult to uniformly apply the ultraviolet-shielding particle coated with silicon oxide to the skin. As a result, a desired sun protection factor (SPF) cannot be obtained.

According to the ultraviolet-shielding particle coated with silicon oxide of the present embodiment, the agglomeration of the ultraviolet-shielding particles coated with silicon oxide is suppressed even when the ultraviolet-shielding particle coated with silicon oxide is applied to an aqueous cosmetic, and the ultraviolet-shielding property is excellent.

According to the ultraviolet-shielding particle coated with silicon oxide of the present embodiment, the agglomeration of the ultraviolet-shielding particles coated with silicon oxide is suppressed even when the ultraviolet-shielding particle coated with silicon oxide is applied to a water phase of an oil-in-water cosmetic, and the ultraviolet-shielding property is excellent.

[Method for Producing Ultraviolet-Shielding Particle Coated with Silicon Oxide]

An example of a method for producing the ultraviolet-shielding particle coated with silicon oxide will be described.

The method for producing the ultraviolet-shielding particle coated with silicon oxide in the present embodiment is, for example, a production method having a surface treatment step of surface-treating the surface of the ultraviolet-shielding particle coated with silicon oxide with a predetermined organic silicon compound.

As the ultraviolet-shielding particle coated with silicon oxide, an ultraviolet-shielding particle coated with silicon oxide produced by a step of mixing a composite particle obtained by coating the surface of an ultraviolet-shielding particle with silicon oxide containing an alkali metal and at least one selected from the group consisting of Mg, Ca, and Ba in a solution including water and substituting the alkali metal that is included in the silicon oxide with at least one selected from the group consisting of Mg, Ca, and Ba (hereinafter, referred to as "substitution step") may also be used.

A step of forming a silicon oxide coat having a higher degree of condensation by adding the ultraviolet-shielding particle coated with silicon oxide containing an alkali metal before the substitution step or the ultraviolet-shielding particle coated with silicon oxide containing at least one selected from the group consisting of Mg, Ca, and Ba after the substitution step, at least one of alkoxysilanes and decamer or lower alkoxysilane oligomers, a catalyst, and water, stirring a mixture thereof for 30 minutes or longer and 24 hours or shorter to cause a reaction, and calcinating a reaction product may also be provided. This step may be carried out separately from or at the same time as the surface treatment step.

Next, a method for producing the ultraviolet-shielding particle coated with silicon oxide will be described in detail.

As the ultraviolet-shielding particle coated with silicon oxide containing an alkali metal, an ultraviolet-shielding particle obtained by reacting a silicate containing an alkali metal such as silicate soda and the ultraviolet-shielding particle to coat the surface of the ultraviolet-shielding particle with silicon oxide may also be used. Alternatively, an ultraviolet-shielding particle coated with a commercially available product of silicon oxide may also be used.

As a method for coating the surface of the ultraviolet-shielding particle with silicon oxide, it is possible to use, for example, methods described in Japanese Laid-open Patent Publication No. H03-183620, Japanese Laid-open Patent Publication No. H11-256133, Japanese Laid-open Patent Publication No. H11-302015, Japanese Laid-open Patent Publication No. 2007-016111, and the like.

The method for coating the surface of the ultraviolet-shielding particle with silicon oxide is selected as necessary, and, for example, the following method is exemplified.

First, the ultraviolet-shielding particles and water are mixed together, and then the ultraviolet-shielding particles are ultrasonic-dispersed in water, thereby preparing an aqueous suspension including the ultraviolet-shielding particles.

Next, the aqueous suspension including the ultraviolet-shielding particles is heated, a sodium silicate aqueous solution is added to the aqueous suspension under stirring, and the aqueous suspension is left to stand for 10 to 60 minutes.

Next, an acid such as diluted sulfuric acid was added to the suspension under stirring to adjust the pH to 5 to 9, and the aqueous suspension is left to stand for 30 minutes to five hours.

Next, this reaction liquid is separated into solid and liquid, the obtained reaction product is cleaned using a solvent such as water and, furthermore, dried at approximately 100° C. to 200° C., thereby obtaining ultraviolet-shielding particles coated with silicon oxide containing an alkali metal.

"Substitution Step"

The substitution step needs to be carried out after a step of coating the surface of the ultraviolet-shielding particle with silicon oxide containing an alkali metal. The reason therefor is that, when a silicate containing an alkali metal and at least one selected from the group consisting of Mg, Ca, and Ba are simply mixed together in a solution including water, the precipitation of at least one of magnesium silicate, calcium silicate, and barium silicate is generated as an impurity. Therefore, the substitution step is preferably placed in any state from after the step of coating the surface of the ultraviolet-shielding particle with silicon oxide through after a drying step by causing a neutralization reaction or the like of the silicate. According to the above-described method, it is possible to reduce a reaction process, and it is possible to produce the ultraviolet-shielding particle coated with silicon oxide in the present embodiment at a low cost.

In the substitution step, first, an ultraviolet-shielding particle coated with silicon oxide containing an alkali metal and at least one selected from the group consisting of Mg, Ca, and Ba are added to and mixed together in a solution including water.

The solution including water is not particularly limited and is selected as necessary. As the solution including water, water or a solution obtained by mixing water and a solvent that is compatible with water are used.

As the solvent that is compatible with water, for example, a protonic polar solvent such as methanol, ethanol, or 2-propanol or an aprotic polar solvent such as acetone or tetrahydrofuran is preferred. Among these, the protonic polar solvent such as methanol, ethanol, or 2-propanol is more preferred.

A reaction temperature in this mixing treatment is not particularly limited and is adjusted as necessary. The reaction temperature needs to be equal to or higher than the solidification point of a solvent in a liquid mixture including the ultraviolet-shielding particle coated with silicon oxide, at least one selected from the group consisting of Mg, Ca, and Ba, and the solution including water.

In addition, the reaction proceeds even when the liquid mixture is left to stand; however, in order to increase the reaction efficiency, the reaction is preferably caused while stirring the liquid mixture.

A reaction time is not particularly limited and is selected as necessary. The reaction time is preferably one hour or longer.

Due to this mixing treatment, the alkali metal in the ultraviolet-shielding particle coated with silicon oxide is substituted with at least one selected from the group consisting of Mg, Ca, and Ba and is eluted from the ultraviolet-shielding particle coated with silicon oxide into the liquid mixture. At least one type of ion selected from the group consisting of Mg, Ca, and Ba that substitutes the alkali metal is incorporated into the ultraviolet-shielding particle coated with silicon oxide by the substitution of the alkali metal, and, consequently, an ultraviolet-shielding particle coated with silicon oxide including at least one selected from the group consisting of Mg, Ca, and Ba is produced.

The content of at least one selected from the group consisting of Mg, Ca, and Ba that is included in the liquid mixture is not particularly limited and is selected as necessary. In order to ion-exchange an alkali ion such as Na or K in the ultraviolet-shielding particle coated with silicon oxide with an ion of at least one selected from the group consisting of Mg, Ca, and Ba, the content of at least one selected from the group consisting of Mg, Ca, and Ba that is included in the liquid mixture is preferably equal to or larger than the total of the molar equivalents of alkali metals in the ultraviolet-shielding particle coated with silicon oxide.

A raw material for providing at least one selected from the group consisting of Mg, Ca, and Ba needs to be an inorganic salt including the above-described element and is not particularly limited. As a raw material for providing Mg, for example, magnesium chloride, magnesium sulfate, magnesium nitrate, and the like are exemplified. As a raw material for providing Ca, for example, calcium chloride, calcium sulfate, and the like are exemplified. As a raw material for providing Ba, for example, barium chloride, barium nitrate, and the like are preferably used.

These raw materials may be used in an intrinsic solid state and may be used in an aqueous solution state.

A substitution step of the alkali metal in the ultraviolet-shielding particle coated with silicon oxide with at least one selected from the group consisting of Mg, Ca, and Ba may also be carried out by separating the liquid mixture containing the ultraviolet-shielding particle coated with silicon oxide generated by the above-described substitution step into solid and liquid and, again, mixing the obtained ultraviolet-shielding particle coated with silicon oxide and at least one selected from the group consisting of Mg, Ca, and Ba in a solution including water. This substitution step may be repeated a plurality of times.

In the case of further densifying the silica coat, at least one of alkoxysilanes and decamer or lower alkoxysilane oligomers and a catalyst may be added to and mixed with the liquid mixture containing the ultraviolet-shielding particle coated with silicon oxide generated by the substitution step and may be thermally treated at 150° C. or higher and lower than 600° C.

"Surface Treatment Step"

The surface treatment step is not particularly limited as long as the substitution treatment is a method capable of treating the surface of an organic silicon compound represented by General Formula (2). In the surface treatment step, a dry-type method or a wet-type method may be used.

$$X_nSi(OR)_{4-n} \qquad (2)$$

(In the formula, X represents an alkyl group, an alkenyl group, or a cycloalkyl group, R represents a hydrogen atom or an alkyl group having 1 to 4 carbon atoms, n represents an integer, and 0<n<4.)

As the surface treatment step, for example, a method of mixing the ultraviolet-shielding particle coated with silicon oxide generated by the substitution step, the organic silicon compound represented by General Formula (2), and a solvent is exemplified. The surface treatment step may be carried out at room temperature or may be carried out by heating.

As specific examples of the organic silicon compound, for example, alkylalkoxysilanes such as methyltrimethoxysilane, methyltriethoxysilane, methyltripropoxysilane, methyltriisopropoxysilane, methyltributoxysilane, ethyltrimethoxysilane, ethyltriethoxysilane, ethyltripropoxysilane, ethyltriisopropoxysilane, ethyltributoxysilane, n-propyltrimethoxysilane, n-propyltriethoxysilane, n-propyltripropoxysilane, n-propyltriisopropoxysilane, n-propyltributoxysilane, isopropyltrimethoxysilane, isopropyltriethoxysilane, isopropyltripropoxysilane, isopropyltriisopropoxysilane, isopropyltributoxysilane, butyltrimethoxysilane, butyltriethoxysilane, butyltripropoxysilane, butyltriisopropoxysilane, sec-butyltrimethoxysilane, sec-butyltriethoxysilane, sec-butyltripropoxysilane, sec-butyltriisopropoxysilane, t-butyltrimethoxysilane, t-butyltriethoxysilane, t-butyltripropoxysilane, and t-Butyltriisopropoxysilane; alkenyl alkoxysilanes such as vinyltrimethoxysilane, vinyltriethoxysilane, vinyltripropoxysilane, and vinyltriisopropoxysilane; and cycloalkylsilanes such as cyclopropyltrimethoxysilane, cyclopropyltriethoxysilane, cyclopropyltripropoxysilane, cyclopropyltriisopropoxysilane, cyclobutyltrimethoxysilane, cyclobutyltriethoxysilane, cyclobutyltripropoxysilane, cyclobutyltriisopropoxysilane, cyclopentyltrimethoxysilane, cyclopentyltriethoxysilane, cyclopentyltripropoxysilane, cyclopentyltriisopropoxysilane, cyclohexyltrimethoxysilane, cyclohexyltriethoxysilane, cyclohexyltripropoxysilane, and cyclohexyltriisopropoxysilane.

Next, the liquid mixture containing the ultraviolet-shielding particle coated with silicon oxide generated by the substitution step is separated into solid and liquid by ordinary pressure filtration, reduced pressure filtration, pressurization filtration, centrifugal separation, and the like. The obtained solid substance is cleaned using a solvent such as water, thereby obtaining an ultraviolet-shielding particle coated with silicon oxide.

The ultraviolet-shielding particle coated with silicon oxide obtained as described above includes water and is thus preferably dried in order to remove the water.

A drying temperature of the ultraviolet-shielding particle coated with silicon oxide is not particularly limited. Generally, the ultraviolet-shielding particle coated with silicon oxide is preferably dried at a temperature of 100° C. or higher. In addition, in the case of drying the ultraviolet-shielding particle coated with silicon oxide at a temperature of 80° C. or lower, reduced pressure drying is preferred.

With the above-described steps, the ultraviolet-shielding particle coated with silicon oxide in the present embodiment can be produced.

In the case of carrying out a step of further densifying the silica coat and the surface treatment step at the same time, the densification step may be carried out, for example, as described below.

At least one of alkoxysilanes and decamer or lower alkoxysilane oligomers, a catalyst, and the organic silicon compound represented by General Formula (2) are added to and mixed with the liquid mixture containing the ultraviolet-shielding particle coated with silicon oxide before the substitution step or the ultraviolet-shielding particle coated with silicon oxide generated by the substitution step. The components may be mixed at room temperature or may be mixed by heating.

Next, this liquid mixture is dried by removing liquid through solid-liquid separation, and the obtained dried substance is thermally treated (calcinated) at 200° C. or higher and lower than 600° C. The ultraviolet-shielding particle coated with silicon oxide in the present embodiment can also be produced.

[Aqueous Composition Containing Ultraviolet-Shielding Particle Coated with Silicon Oxide]

An aqueous composition containing the ultraviolet-shielding particle coated with silicon oxide of the present embodiment contains the ultraviolet-shielding particle coated with silicon oxide and water.

The water is not particularly limited as long as the water is water that is ordinarily used for cosmetics, and pure water, ion-exchange water, distilled water, purified water, ultrapure water, natural water, alkali ion water, deep-water, and the like are used.

The content of the water in the aqueous composition containing the ultraviolet-shielding particle coated with silicon oxide is appropriately adjusted depending on desired characteristics. From the viewpoint of improving the sensation of the aqueous composition containing the ultraviolet-shielding particle coated with silicon oxide, the content of the water is preferably 10% by mass or more and 99% by mass or less, more preferably 20% by mass or more and 95% by mass or less, and still more preferably 40% by mass or more and 94% by mass or less.

In the aqueous composition containing the ultraviolet-shielding particle coated with silicon oxide of the present embodiment, the average dispersed particle diameter of the ultraviolet-shielding particles coated with silicon oxide is preferably 10 nm or larger and 2 μm or smaller, more preferably 20 nm or larger and 800 nm or smaller, and still more preferably 25 nm or larger and 500 nm or smaller.

When the average dispersed particle diameter of the ultraviolet-shielding particles coated with silicon oxide is 10 nm or larger, there is no case where the crystallinity of the ultraviolet-shielding particle coated with silicon oxide decreases, and thus a sufficient ultraviolet-shielding property can be exhibited. On the other hand, when the average dispersed particle diameter of the ultraviolet-shielding particles coated with silicon oxide is 2 μm or smaller, there is no case where a glare, a squeak, and the like are generated, a texture of using a cosmetic into which the ultraviolet-shielding particles coated with silicon oxide is formulated improves, dispersion stability improves, and a stable composition is obtained.

In the present embodiment, the average dispersed particle diameter refers to the average value of secondary particle diameters measured by a dynamic light scattering method.

From the viewpoint of obtaining a transparent aqueous composition containing the ultraviolet-shielding particle coated with silicon oxide, the average dispersed particle diameter is preferably 10 nm or larger and 200 nm or smaller.

The content of the ultraviolet-shielding particle coated with silicon oxide in the aqueous composition containing the ultraviolet-shielding particle coated with silicon oxide of the present embodiment needs to be appropriately adjusted in order to obtain desired ultraviolet-shielding performance and is not particularly limited. The content of the ultraviolet-shielding particle coated with silicon oxide is preferably 1% by mass or more and 80% by mass or less, more preferably 20% by mass or more and 70% by mass or less, and still more preferably 30% by mass or more and 60% by mass or less.

Here, the content of the ultraviolet-shielding particle coated with silicon oxide was determined to be preferably 1% by mass or more and 80% by mass or less. The reason therefor is as described below. When the content of the ultraviolet-shielding particle coated with silicon oxide is 1% by mass or more, the aqueous composition containing the ultraviolet-shielding particle coated with silicon oxide is capable of exhibiting sufficient ultraviolet-shielding performance. As a result, it is not necessary to add a large amount of the aqueous composition containing the ultraviolet-shielding particle coated with silicon oxide in order to exhibit desired ultraviolet-shielding performance at the time of blending the aqueous composition containing the ultraviolet-shielding particle coated with silicon oxide into a cosmetic or the like, and an increase in the manufacturing cost can be suppressed. On the other hand, when the content of the ultraviolet-shielding particle coated with silicon oxide is 80% by mass or less, there is no case where the viscosity of the aqueous composition containing the ultraviolet-shielding particle coated with silicon oxide increases, the dispersion stability of the ultraviolet-shielding particle coated with silicon oxide is maintained, and the sedimentation of the ultraviolet-shielding particle coated with silicon oxide can be suppressed.

The pH of the aqueous composition containing the ultraviolet-shielding particle coated with silicon oxide of the present embodiment may be adjusted to 6 to 7 by adding a weak acid or a pH buffer solution that is used for cosmetics such as citric acid. The pH of the composition can be maintained at 7 or lower for a long period of time by adding the above-described weak acid.

The aqueous composition containing the ultraviolet-shielding particle coated with silicon oxide of the present embodiment may include ordinarily-used additives such as a dispersant, a stabilizer, a water-soluble binder, a water-soluble vinyl polymer, a viscosity improver, and alcohols as long as the characteristics are not impaired.

From the viewpoint of improving the dispersion stability of the aqueous composition, the aqueous composition preferably contains at least one of a water-soluble vinyl polymer and alcohols.

As the dispersant, an anionic surfactant, a cationic surfactant, an ampholytic surfactant, a nonionic surfactant, a silane coupling agent such as organoalkoxysilane or organochlorosilane, or a modified silicone such as polyether-modified silicone or amino-modified silicone is preferably used. The type or amount of the dispersant may be appropriately selected depending on the particle diameter of the ultraviolet-shielding particle coated with silicon oxide or an intended type of a dispersion medium, and only one dispersant may be singly used or two or more dispersants may be used in mixture.

As the water-soluble binder, it is possible to use polyvinyl alcohol (PVA), polyvinylpyrrolidone, hydroxyl cellulose, polyacrylic acid, or the like.

The water-soluble vinyl polymer is not particularly limited as long as the water-soluble vinyl polymer is a vinyl polymer that can be mixed with water at an arbitrary ratio and can be used for cosmetics.

As such a water-soluble vinyl polymer, it is possible to use a carboxy vinyl polymer, an alkyl-modified carboxy vinyl polymer, an alkyl acrylate/methacrylic acid/polyoxyethylene copolymer, or the like. These water-soluble vinyl polymers may be used singly or two or more water-soluble vinyl polymers may be used in combination.

As the carboxy vinyl polymer, for example, carboxy vinyl polymers known under the trade names of Carbopol (registered trademark) 940, Carbopol (registered trademark) 941, Carbopol (registered trademark) 980, Carbopol (registered trademark) 981, and Carbopol (registered trademark) Ultrez10 (manufactured by Lubrizol Advanced Materials) are exemplified.

As the alkyl-modified carboxy vinyl polymer, for example, alkyl-modified carboxy vinyl polymers known under the trade names of Carbopol (registered trademark) 1342, PEMULEN (registered trademark) TR-1, and PEMULEN (registered trademark) TR-2 (manufactured by Lubrizol Advanced Materials) are exemplified.

As the alkyl acrylate/methacrylic acid/polyoxyethylene copolymer, for example, an (acrylate/Steareth-20 methacrylate) copolymer, an (acrylate/Bekhnes-25 methacrylate) copolymer, and an (acrylate/Steareth-20 methacrylate) crosspolymer are exemplified. In addition, as the alkyl acrylate/methacrylic acid/polyoxyethylene copolymer, ACULYN (registered trademark) 22, ACULYN (registered trademark) 28, and ACULYN (registered trademark) 88, which are commercially available from Rohm and Haas Corporate.

Among these alkyl acrylate/methacrylic acid/polyoxyethylene copolymers, an ACULYN (registered trademark) 22 (acrylate/Steareth-20 methacrylate) copolymer is particularly preferred since this copolymer is not sticky and imparts favorable sensation.

In a case where the aqueous composition containing the ultraviolet-shielding particle coated with silicon oxide of the present embodiment contains the water-soluble vinyl polymer, the content of the water-soluble vinyl polymer with respect to 100 parts by mass of the ultraviolet-shielding particle coated with silicon oxide is preferably 0.02 parts by mass or more and 6.0 parts by mass or less, more preferably 0.1 parts by mass or more and 5.0 parts by mass or less, and still more preferably 0.2 parts by mass or more and 4.5 parts by mass or less.

When the content of the water-soluble vinyl polymer with respect to 100 parts by mass of the ultraviolet-shielding particle coated with silicon oxide is 0.02 parts by mass or more, dispersion stability is ensured, and a homogeneous composition is obtained. On the other hand, when the content of the water-soluble vinyl polymer with respect to 100 parts by mass of the ultraviolet-shielding particle coated with silicon oxide is 6.0 parts by mass or less, the viscosity falls in an appropriate range, and stirring is easy, and thus a homogeneous composition is obtained.

In addition, in the aqueous composition containing the ultraviolet-shielding particle coated with silicon oxide, the content of the water-soluble vinyl polymer is preferably 0.01% by mass or more and 1.0% by mass or less, more preferably 0.05% by mass or more and 0.75% by mass or less, and still more preferably 0.1% by mass or more and 0.5% by mass or less.

In the aqueous composition containing the ultraviolet-shielding particle coated with silicon oxide of the present embodiment, the total content of the respective components is 100% by mass, and there is no case where the total content of the respective components exceeds 100% by mass.

The viscosity improver is not particularly limited as long as the viscosity improver is used for cosmetics in the case of applying the aqueous composition containing the ultraviolet-shielding particle coated with silicon oxide of the present embodiment to cosmetics. As the viscosity improver, for example, natural water-soluble polymers such as gelatin, casein, collagen, hyaluronic acid, albumin, and starch, semi-synthetic polymers such as methylcellulose, ethylcellulose, methylhydroxypropylcellulose, carboxymethylcellulose, hydroxymethylcellulose, hydroxypropylcellulose, sodium carboxymethylcellulose, and propylene glycol alginate, synthetic polymers such as polyvinyl alcohol, polyvinyl pyrrolidone, a carbomer (carboxy vinyl polymer), polyacrylate, and polyethylene oxide, inorganic minerals such as bentonite, laponite, and hectorite, and the like are preferably used. These viscosity improvers may be used singly or two or more viscosity improvers may be used in combination.

Among these viscosity improvers, the synthetic polymers are preferred, and carbomer (carboxy vinyl polymer) is more preferred.

Here, in a case where a carbomer is used as the viscosity improver, the content of the carbomer in the aqueous composition containing the ultraviolet-shielding particle coated with silicon oxide of the present embodiment is preferably 0.01% by mass or more and 10% by mass or less and more preferably 0.01% by mass or more and 3% by mass or less.

When the content of the carbomer in the aqueous composition containing the ultraviolet-shielding particle coated with silicon oxide of the present embodiment is 0.01% by mass or more, a viscosity-improving effect can be obtained. When the content of the carbomer is 10% by mass or less, it is possible to suppress an excessive increase in the viscosity of the aqueous composition containing the ultraviolet-shielding particle coated with silicon oxide, and thus, in a case where the aqueous composition is applied to a cosmetic, the cosmetic spreads well on skin when applied with a brush, and there is no disadvantage of the degradation of the sensation and the like.

In addition, in a case where a carbomer is used as the viscosity improver, the hydrogen-ion exponent (pH) of the carbomer in the aqueous composition containing the ultraviolet-shielding particle coated with silicon oxide of the present embodiment is preferably 5 or higher and 10 or lower, more preferably 6 or higher and 10 or lower, and still more preferably 7 or higher and 9 or lower. When the pH in the aqueous composition containing the ultraviolet-shielding particle coated with silicon oxide of the present embodiment is set to be in the above-described range, a change in the viscosity and the like over time can be suppressed.

The alcohols are not particularly limited as long as the alcohols can be used for cosmetics, and it is possible to use, for example, monovalent alcohols or polyvalent alcohols having 1 to 6 carbon atoms such as ethanol, 1-propanol, 2-propanol, 1-butanol, 2-butanol, octanol, glycerin, 1,3-butylene glycol, propylene glycol, and sorbitol.

Among these alcohols, glycerin is preferred since glycerin is broadly used in cosmetics due to its effect for improving the texture of the cosmetics or moisturization.

In a case where the aqueous composition containing the ultraviolet-shielding particle coated with silicon oxide of the present embodiment contains the alcohols, the content of the alcohols with respect to 100 parts by mass of the ultraviolet-shielding particle coated with silicon oxide is preferably 10 parts by mass or more and 100 parts by mass or less and more preferably 20 parts by mass or more and 50 parts by mass or less.

When the content of the alcohols with respect to 100 parts by mass of the ultraviolet-shielding particle coated with silicon oxide is 10 parts by mass or more, it is possible to further improve the dispersibility of the ultraviolet-shielding particle coated with silicon oxide. When the content of the alcohols with respect to 100 parts by mass of the ultraviolet-shielding particle coated with silicon oxide is 100 parts by mass or less, it is possible to suppress the deterioration of stickiness or texture at the time of blending the aqueous composition containing the ultraviolet-shielding particle coated with silicon oxide of the present embodiment into cosmetics.

In addition, in the aqueous composition containing the ultraviolet-shielding particle coated with silicon oxide of the present embodiment, the content of the alcohols is preferably 0.1% by mass or more and 30% by mass or less, more preferably 0.3% by mass or more and 25% by mass or less, and still more preferably 0.5% by mass or more and 20% by mass or less.

In the aqueous composition containing the ultraviolet-shielding particle coated with silicon oxide of the present embodiment, a value obtained by dividing the viscosity under an acceleration condition, for example, the viscosity measured after the elapsing of 300 hours in the case of storing the aqueous composition at 40° C. by the viscosity after a decrease in the viscosity under an initial condition, for example, the viscosity after 15 hours is preferably 0.8 or higher and 1.2 or lower. When the value obtained by dividing the viscosity under an acceleration condition, that is, after 300 hours by the viscosity after a decrease in the initial viscosity is set to be in the above-described range as described above, it is possible to maintain the viscosity of the aqueous composition containing the ultraviolet-shielding particle coated with silicon oxide of the present embodiment for a medium or long period of time.

In a case where the content of the ultraviolet-shielding particle coated with silicon oxide in the aqueous composition containing the ultraviolet-shielding particle coated with silicon oxide of the present embodiment is set to 5% by mass, and a coated film having a thickness of 12 μm is formed using this composition, the transmittance of this coated film for light having a wavelength of 450 nm is preferably 40% or higher, more preferably 45% or higher, and still more preferably 50% or higher.

In addition, the sun protection factor (SPF) value of this coated film is preferably 6.0 or higher and more preferably 6.5 or higher.

The transmittance and SPF value of the coated film can be obtained by applying the aqueous composition containing the ultraviolet-shielding particle coated with silicon oxide containing 5% by mass of the ultraviolet-shielding particle coated with silicon oxide onto a silica substrate using a bar coater to form a coated film having a thickness of 12 μm and measuring the spectral transmittance of the coated film using an SPF analyzer UV-1000S (manufactured by Labsphere).

In addition, an absorption spectrum is calculated from this transmittance, the area of the absorption spectrum from 290 nm toward the longer wavelength is integrated, and a wavelength at which the integrated area reaches 90% of an area integrated from 290 nm through 400 nm can be calculated as a critical wavelength. As the wavelength at which the critical wavelength is present increases, UVA-shielding performance further enhances, and the critical wavelength is preferably 375 nm or longer, more preferably 378 nm or longer, and still more preferably 380 nm or longer.

A method for producing the aqueous composition containing the ultraviolet-shielding particle coated with silicon oxide of the present embodiment is not particularly limited as long as the ultraviolet-shielding particle coated with silicon oxide can be dispersed in water.

As a dispersion method that can be used for such dispersion, a dispersion method using a well-known dispersion device can be used. A dispersion method using, for example, a stirrer, additionally, a beads mill using zirconia beads, a ball mill, a homogenizer, an ultrasonic disperser, a kneader, a three-roll mill, a rotation and revolution mixer, or the like as the dispersion device is preferably used.

A time necessary for a dispersion treatment needs to be a time long enough to uniformly disperse the ultraviolet-shielding particle coated with silicon oxide in water.

According to the aqueous composition containing the ultraviolet-shielding particle coated with silicon oxide of the present embodiment, since the ultraviolet-shielding particle coated with silicon oxide of the present embodiment is included, the ultraviolet-shielding property is excellent even when the aqueous composition is applied to an aqueous cosmetic.

[Cosmetic]

A cosmetic of the present embodiment is obtained by containing at least one of the ultraviolet-shielding particle coated with silicon oxide of the present embodiment and the aqueous composition containing the ultraviolet-shielding particle coated with silicon oxide of the present embodiment and a cosmetic product base raw material.

The cosmetic of the present embodiment preferably contains water.

Here, the cosmetic product base raw material refers to a variety of raw materials that form the main body of a cosmetic product, and an oil-based raw material, an aqueous raw material, a surfactant, a powder raw material, and the like are exemplified.

As the oil-based raw material, for example, fats and oils, higher aliphatic acids, higher alcohols, ester oils, and the like are exemplified.

As the aqueous raw material, purified water, alcohols, viscosity improvers, and the like are exemplified.

As the powder raw material, organic pigments, white pigments, pearl agents, extender pigments, and the like are exemplified.

The cosmetic of the present embodiment can be obtained by, for example, blending the ultraviolet-shielding particle coated with silicon oxide of the present embodiment or the aqueous composition containing the ultraviolet-shielding particle coated with silicon oxide of the present embodiment into the cosmetic product base raw material such as a milk lotion, a cream, a foundation, a lipstick, a blush, or an eye shadow using a well-known method.

In addition, the cosmetic of the present embodiment can also be obtained by blending the ultraviolet-shielding particle coated with silicon oxide of the present embodiment or the aqueous composition containing the ultraviolet-shielding particle coated with silicon oxide of the present embodiment into an oil phase or a water phase to produce an O/W or W/O-type emulsion and then blending the emulsion with the cosmetic product base raw material.

The content of the ultraviolet-shielding particle coated with silicon oxide in the cosmetic needs to be appropriately adjusted depending on a desired characteristic, and, for example, the lower limit of the content of the ultraviolet-shielding particle coated with silicon oxide may be 0.01% by mass or more, may be 0.1% by mass or more, or may be 1% by mass or more. In addition, the upper limit of the content of the ultraviolet-shielding particle coated with silicon oxide may be 50% by mass or less, may be 40% by mass or less, or may be 30% by mass or less.

According to the cosmetic of the present embodiment, at least one of the ultraviolet-shielding particle coated with silicon oxide of the present embodiment and the aqueous composition containing the ultraviolet-shielding particle coated with silicon oxide of the present embodiment is contained, and thus the ultraviolet-shielding property is excellent.

[Oil-in-Water Cosmetic]

An oil-in-water cosmetic of the present embodiment is obtained by containing at least one of the ultraviolet-shielding particle coated with silicon oxide of the present embodiment and the aqueous composition containing the ultraviolet-shielding particle coated with silicon oxide of the present embodiment in a water phase.

The oil-in-water cosmetic of the present embodiment is an oil-in-water emulsion including at least one of the ultraviolet-shielding particle coated with silicon oxide of the present embodiment and the aqueous composition containing the ultraviolet-shielding particle coated with silicon oxide of the present embodiment in a water phase and containing an oil component in an oil phase.

The water phase may include additives that are ordinarily used for aqueous cosmetics such as a dispersant, a stabilizer, a water-soluble binder (water-soluble polymer), a viscosity improver, and an alcohol as necessary.

The oil phase may appropriately include additives that are ordinarily used for cosmetics such as an oil-soluble preservative, an ultraviolet absorber, an oil-soluble chemical, an oil-soluble dye, an oil-soluble protein, a plant oil, an animal oil, and a solvent as necessary.

The oil component is not particularly limited as long as the oil component can be used for cosmetics, and an oil component capable of dissolving a desired organic ultraviolet-shielding agent is appropriately selected.

As such an oil component, an oil component containing at least one selected from the group consisting of a higher alcohol, a higher aliphatic acid, and an aliphatic ester formed by bonding a higher alcohol and a higher aliphatic acid is preferred. When the oil component contains these components, skin tension or a moisturized feeling improves, and the sustainability of this effect improves. In addition, a liquid organic ultraviolet absorber such as ethylhexyl methoxycinnamate can also be used as the oil component.

As the higher alcohol, for example, capryl alcohol, lauryl alcohol, stearyl alcohol, oleyl alcohol, myristyl alcohol, cetyl alcohol, cholesterol, phytosterol, and the like are preferably used. These higher alcohols may be used singly or two or more higher alcohols may be used in combination.

As the higher aliphatic acid, for example, saturated or unsaturated aliphatic acids having 12 to 24 carbon atoms are preferably used, and, for example, myristic acid, palmitic acid, stearic acid, isostearic acid, linoleic acid, arachidonic acid, and the like are preferably used. These higher aliphatic acids may be used singly or two or more higher aliphatic acids may be used in combination.

As the aliphatic ester, for example, cetyl myristate, octyldodecyl myristate, isopropyl myristate, myristyl myristate, 2-hexyldecyl myristate, octyl palmitate, isopropyl palmitate, butyl stearate, stearyl stearate, octyl stearate, isocetyl stearate, glycol distearate, cetyl 2-ethylhexanoate, 2-ethylhexyl stearate, stearyl stearate, cholesteryl isostearate, isocetyl isostearate, isononyl isononanoate, ethyl oleate, decyl oleate, oleyl oleate, diisopropyl sebacate, dioctyl sebacate, hexyldecyl dimethyl octanoate, cetyl octanoate, neopentyl glycol dioctanoate, hexyl laurate, pentaerythritol tetraoctanoate, and the like are preferably used. These aliphatic esters may be used singly or two or more aliphatic esters may be used in combination.

In the present embodiment, from the viewpoint of controlling the separation of the water phase and the oil phase, the ester value of the aliphatic acid ester is preferably low. Specifically, as the aliphatic acid ester, an aliphatic acid ester having an ester value of 95 to 170 is preferably used. As such an aliphatic acid ester, for example, octyldodecyl myristate (having an ester value of 100 to 111), cetyl 2-ethylhexanoate (having an ester value of 135 to 160), and the like are exemplified.

The oil-in-water cosmetic of the present embodiment preferably contains a chelator.

When the oil-in-water cosmetic contains a chelator, it is possible to further suppress a change in the hydrogen exponent of the oil-in-water cosmetic over time.

The chelator is not particularly limited as long as the chelator is used for cosmetics. As the chelator, for example, ethylenediaminetetraacetic acid (EDTA), ethylene glycoldiaminetetraacetic acid, diethylenetriaminepentaacetic acid, citric acid, phytic acid, polyphosphoric acid, metaphosphoric acid, and the like are used. Among these, ethylenediaminetetraacetic acid (EDTA) is preferred from the viewpoint of high versatility.

The content of the chelator in the oil-in-water cosmetic is appropriately adjusted in line with desired performance and is, for example, preferably 0.01% by mass or more and 1.0% by mass or less.

Here, when the content of the chelator is 0.01% by mass or more, a desired characteristic can be obtained in the oil-in-water cosmetic. When content of the chelator is 1.0% by mass or less, it is possible to safely use the oil-in-water cosmetic. For example, the amount of ethylenediaminetetraacetic acid (EDTA) blended into the cosmetic is regulated to be 1.0% by mass or less in The Japanese Standards of Quasi-Drug Ingredients Consolidated Edition.

The oil-in-water cosmetic of the present embodiment preferably contains an organic ultraviolet-shielding agent in the oil phase.

The organic ultraviolet-shielding agent is not particularly limited as long as the organic ultraviolet-shielding agent is used for cosmetics. As the organic ultraviolet-shielding agent, for example, anthranilates, cinnamic acid derivatives, salicylic acid derivatives, camphor derivatives, benzophenone derivatives, β,β'-diphenylacrylate derivatives, benzotriazole derivatives, benzalmalonate derivatives, benzoimidazole derivatives, imidazolines, bisbenzoazolyl derivatives, p-aminobenzoic acid (PABA) derivatives, methylene bis(hydroxyphenyl benzotriazole) derivatives, TINUVIN, and the like are exemplified. As the organic ultraviolet-shielding agent, at least one selected from the above-described group is used.

The average dispersed particle diameter of the ultraviolet-shielding particles coated with silicon oxide in the oil-in-water cosmetic of the present embodiment is preferably 10 nm or larger and 2 μm or smaller, more preferably 20 nm or larger and 800 nm or smaller, and still more preferably 25 nm or larger and 500 nm or smaller.

When the average dispersed particle diameter of the ultraviolet-shielding particles coated with silicon oxide is 10 nm or larger, there is no case where the crystallinity of the ultraviolet-shielding particle coated with silicon oxide decreases, and thus a sufficient ultraviolet-shielding property can be exhibited. On the other hand, when the average dispersed particle diameter of the ultraviolet-shielding particles coated with silicon oxide is 2 μm or smaller, there is no case where a glare, a squeak, and the like are generated, a texture of using a cosmetic improves, dispersion stability improves, and a stable oil-in-water cosmetic is obtained.

The oil-in-water cosmetic of the present embodiment may be used in a form of a milk lotion, a cream, a sunscreen, a foundation, a serum, a makeup base material, a lipstick, or the like when, in addition to the above-described components, other components are appropriately added thereto.

As the other components, an inorganic ultraviolet-shielding agent such as zinc oxide or titanium oxide, an organic ultraviolet-shielding agent, an additive that is ordinarily used for cosmetics such as a whitening agent or a viscosity improver, a cosmetic product base raw material, and the like are exemplified.

The oil-in-water cosmetic of the present embodiment contains at least one of the ultraviolet-shielding particle coated with silicon oxide of the present embodiment and the aqueous composition containing the ultraviolet-shielding particle coated with silicon oxide of the present embodiment and is thus excellent in terms of an ultraviolet-shielding property.

[Method for Producing Oil-in-Water Cosmetic]

A method for producing the oil-in-water cosmetic of the present embodiment is not particularly limited as the method for producing the oil-in-water cosmetic is a method in which an oil-in-water (O/W) cosmetic containing at least one of the ultraviolet-shielding particle coated with silicon oxide of the present embodiment and the aqueous composition containing the ultraviolet-shielding particle coated with silicon oxide of the present embodiment in a water phase and containing an oil component in an oil phase can be produced.

For example, water, the aqueous composition containing the ultraviolet-shielding particle coated with silicon oxide of the present embodiment, a pH adjuster, and an emulsifier are mixed together in advance, thereby producing a mixture for a water phase. In addition, an oil component is added to and mixed with the mixture for a water phase to produce an oil-in-water emulsion, whereby the oil-in-water cosmetic of the present embodiment can be produced.

In a case where the aqueous composition containing the ultraviolet-shielding particle coated with silicon oxide contains an alkyl-modified carboxy vinyl polymer or an alkyl acrylate/methacrylic acid/polyoxyethylene copolymer, an alkyl portion plays a role of an emulsifier, and thus an emulsifier may not be added to the aqueous composition.

The emulsifier is not particularly limited as long as the emulsifier can be used in a cosmetic in order to produce an oil-in-water emulsion. For example, a hydrophilic surfactant can be preferably used, and, as the hydrophilic surfactant, glycerin, glycerin aliphatic acid ester, polyglycerin aliphatic acid esters, polyoxyethylene glycerin aliphatic acid ester, sorbitan aliphatic acid ester, propylene glycol aliphatic acid esters, polyoxyethylene (hereinafter, abbreviated as "POE") sorbitan aliphatic acid esters, POE sorbit aliphatic acid esters, POE glycerin aliphatic acid esters, POE aliphatic acid esters, POE alkyl ethers, POE alkyl phenyl ethers, POE castor oil, POE alkylamine, POE aliphatic acid amide, and the like are exemplified.

In the case of adding the organic ultraviolet-shielding agent to the aqueous composition, the organic ultraviolet-shielding agent may be mixed with the mixture for a water phase and emulsified after the oil component and the organic ultraviolet-shielding agent are mixed together in advance.

EXAMPLES

Hereinafter, the present invention will be specifically described using examples and comparative examples, but the present invention is not limited by these examples.

Example 1

Zinc oxide particles (average particle diameter: 35 nm, manufactured by Sumitomo Osaka Cement Co. Ltd.) ad water were mixed together, next, ultrasonic dispersion was carried out, and a zinc oxide aqueous suspension containing 20% by mass of zinc oxide was prepared.

Next, this zinc oxide aqueous suspension was added to a silicate soda aqueous solution including 20% by mass of silicate soda in terms of silicon oxide with respect to the mass of the zinc oxide particles in the zinc oxide aqueous suspension and strongly stirred, thereby producing a suspension.

Next, this suspension was heated to 60° C., and the pH was adjusted to 6.5 to 7 by gradually adding diluted hydrochloric acid while stirring the suspension. After that, the suspension was left to stand for two hours, and then, furthermore, the same mass of a calcium chloride aqueous solution (25% by mass of calcium chloride dihydrate) as the mass of the zinc oxide particles in the suspension was added thereto and stirred, and, furthermore, the mixture was left to stand for two hours.

Next, this suspension was separated into solid and liquid using a centrifugal separator, and the obtained solid substance was cleaned with water. After that, this solid substance was dried at 150° C. and, furthermore, thermally treated (calcinated) at 500° C. for two hours, thereby producing zinc oxide coated with silicon oxide.

Next, this zinc oxide coated with silicon oxide and 2-propanol were mixed together, and then the mixture was ultrasonic-dispersed, thereby producing a zinc oxide coated with silicon oxide 2-propanol suspension containing 10% by mass of the zinc oxide coated with silicon oxide.

Next, this suspension was heated to 60° C., and the pH of the suspension was adjusted to 10 to 11 by adding ammonia and water while stirring the suspension. The amount of water added was set so as to be 120% by mass of tetraethoxysilane in a tetraethoxysilane 2-propanol aqueous solution that was added later.

Furthermore, the tetraethoxysilane 2-propanol aqueous solution was slowly added dropwise to this suspension so that the amount of tetraethoxysilane added dropwise reached 15% by mass of the total mass of the zinc oxide in terms of silicon oxide.

Next, methyltriethoxysilane was slowly added dropwise to this suspension so that the content reached 0.5% by mass (the content of an alkyl group in the zinc oxide particles coated with silicon oxide reached 0.04% by mass) of the total mass of the zinc oxide particles, and the components were continuously stirred for six hours.

After the end of a reaction, this suspension was separated into solid and liquid using a centrifugal separator, and the obtained solid substance was dried at 150° C. Next, this dried substance was thermally treated (calcinated) at 500° C. for three hours, thereby obtaining zinc oxide particles coated with silicon oxide of Example 1.

"Production of Aqueous Composition Containing Zinc Oxide Particles Coated with Silicon Oxide"

46.0 Parts by mass of a gel which was obtained by mixing water and 0.2 parts by mass of an alkyl-modified carboxy vinyl polymer (trade name: PEMULEN TR-1, manufactured by Lubrizol Advanced Materials) and had a pH adjusted to 6.0 using 2.5 mol/L of sodium hydroxide, 50 parts by mass of the obtained zinc oxide particles coated with silicon oxide of Example 1, and 4.0 parts by mass of glycerin were mixed together using a homogenizing disper, thereby obtaining an aqueous composition containing the zinc oxide particles coated with silicon oxide of Example 1.

[Evaluation of Dispersibility of Zinc Oxide Particles Coated with Silicon Oxide in Aqueous Composition]

1.5 Gram of a carbomer (trade name: Carbopol Ultrez 10 polymer, manufactured by Lubrizol Advanced Materials) was dissolved in pure water, and then a 10% by mass sodium hydroxide aqueous solution was added dropwise thereto, thereby obtaining a carboxy vinyl polymer gel containing 1.5% by mass of the carbomer and having a pH of 7.5.

10 Parts by mass of the aqueous composition containing the zinc oxide particles coated with silicon oxide of Example 1 and 90 parts by mass of the obtained carboxy vinyl polymer gel were mixed together. This liquid mixture was sandwiched by two glass slides and observed using an optical microscope.

As a result, the maximum particle diameter in an observed agglomerate of the zinc oxide particles coated with silicon oxide was 20 μm. The result is shown in FIG. 1 and Table 1.

[Evaluation of Surface Wettability of Zinc Oxide Particles Coated with Silicon Oxide]

The zinc oxide particles coated with silicon oxide of Example 1 and decamethylcyclopentasiloxane were mixed together in a mass ratio of 1:1 and dispersed for 10 minutes using an ultrasonic cleaning machine ((W-113MK-II, manufactured by Honda Electronics Co., Ltd.), thereby preparing a liquid mixture. Next, this liquid mixture was left to stand for 20 hours.

As a result of visually observing the liquid mixture that had been left to stand, the liquid mixture was separated into a water phase and an oil phase, the water phase in which the zinc oxide particles coated with silicon oxide were dispersed became white-turbid, and the oil phase was transparent.

The spectral transmittance of the oil phase in the liquid mixture was measured using an SPF analyzer UV-1000S (manufactured by Labsphere) with reference to decamethylcyclopentasiloxane. As a result, it was confirmed that the transmittance at 360 nm was 100% and the surface state of the zinc oxide particle coated with silicon oxide of Example 1 was readily absorbed by water but not readily absorbed by oil.

[Evaluation of SPF of Aqueous Composition]

Figure 2:
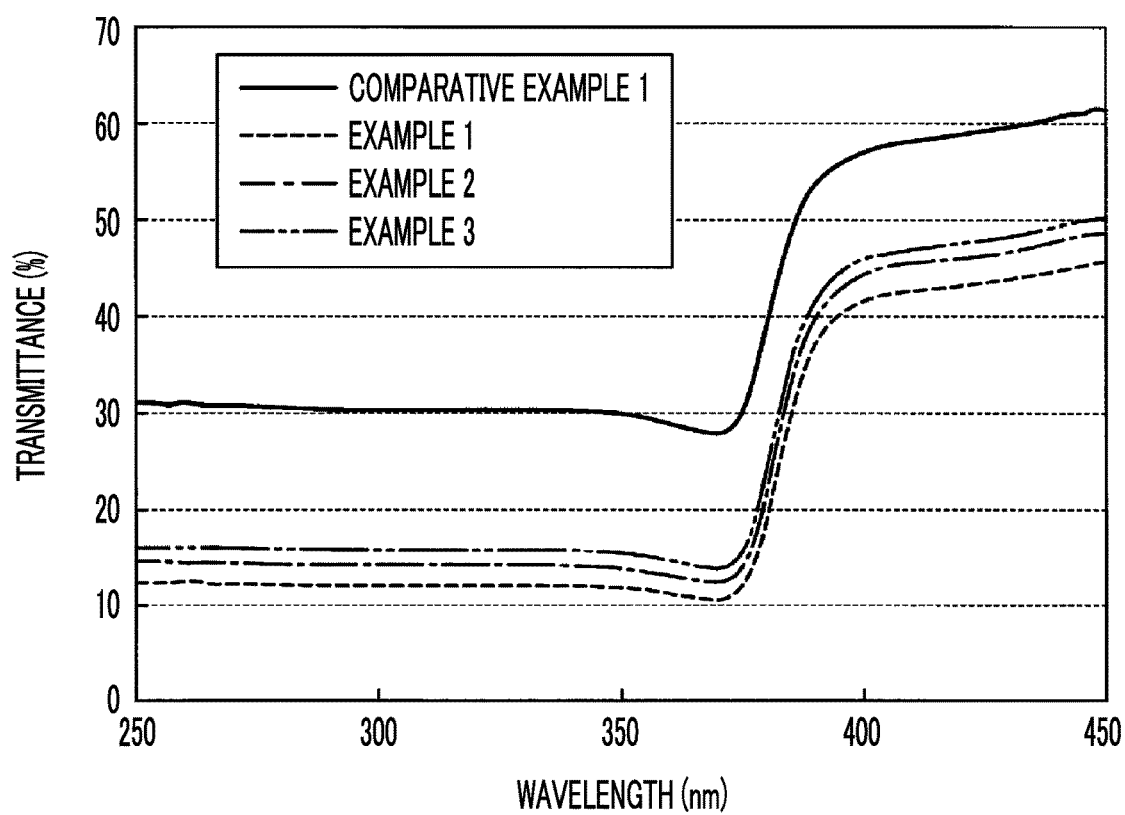
FIG. 2 is a graph showing spectral transmittances of aqueous compositions containing zircon oxide particles coated with silicon oxide of Examples 1 to 3 and Comparative Example 1.

10 Parts by mas of the aqueous composition containing the zircon oxide particles coated with silicon oxide of Example 1 and 90 parts by mass of the carboxy vinyl polymer gel having a pH of 7.5 were mixed together in the same manner as in the above-described "evaluation of dispersibility of zinc oxide particles coated with silicon oxide in aqueous composition". A thin film was formed on a silica substrate using the liquid mixture so that the thickness reached 12 μm, and the spectral transmittance of the thin film was measured using an SPF analyzer UV-1000S (manufactured by Labsphere). The result is shown in FIG. 2. The SPF value was 8.2.

[Evaluation of Stability of Viscosity of Aqueous Composition]

The pH and the viscosity of the aqueous composition containing the zircon oxide particles coated with silicon oxide of Example 1 immediately after being produced (zero hours) were measured. This composition was stored at 40° C., and the pH and the viscosity were measured every predetermined hours. The result is shown in Table 2 and FIG. 3.

"Production of Oil-in-Water Cosmetic"

79.1 parts by mass of water, 0.6 parts by mass of PEG-60 hydrogenated castor oil, and 0.3 parts by mass of an alkyl-modified carboxy vinyl polymer (trade name: PEMULEN TR-1, manufactured by Lubrizol Advanced Materials) were mixed together.

Next, 1.8 mol/L of potassium hydroxide was mixed into this mixture, thereby adjusting the pH to 7.0 and producing a gel.

Next, 10.0 parts by mass of ethylhexyl methoxycinnamate was added to the obtained gel, and the components were mixed together using a homogenizing disper.

Next, 10.0 parts by mass of the aqueous composition containing the zircon oxide particles coated with silicon oxide of Example 1 was added to the obtained mixture, and the components were mixed together using a homogenizing disper, thereby obtaining an oil-in-water cosmetic of Example 1 containing the aqueous composition containing the zircon oxide particles coated with silicon oxide in a water phase.

[Evaluation of Dispersibility of Zinc Oxide Particles Coated with Silicon Oxide in Oil-in-Water Cosmetic]

"Production of Synthetic Sebum"

5.0 Parts by mass of oleic acid, 5.0 parts by mass of squalene, and 5.0 parts by mass of olive oil were mixed together, thereby producing a synthetic sebum.

"Evaluation of Dispersibility"

6.5 Parts by mass of the oil-in-water cosmetic of Example 1 and 2.5 parts by mass of the synthetic sebum were mixed together. This liquid mixture was sandwiched by two glass slides and observed using an optical microscope.

Figure 7:
FIG. 7 is a view showing an optical microscopic image of an oil-in-water cosmetic of Example 1.

As a result, the maximum particle diameter in an observed agglomerate of the zinc oxide particles coated with silicon oxide was 25 μm. The result is shown in FIG. 7.

[Evaluation of Ultraviolet-Shielding Property]

The synthetic sebum produced above was applied to a Helioplate (trade name: HELIOPLATE HD6, manufactured by Helioscreen) so as to reach 0.5 mg/cm$^2$ and dried for 30 minutes.

Next, the oil-in-water cosmetic of Example 1 was applied so as to be 1.3 mg/cm$^2$ and dried for 15 minutes, thereby forming a coated film. The SPF value of this coated film was measured using an SPF analyzer UV-1000S (manufactured by Labsphere).

As a result, the SPF value was 13.3.

Example 2

Zinc oxide particles coated with silicon oxide of Example 2 were obtained in the same manner as in Example 1 except for the fact that, in Example 1, the content of methyltriethoxysilane reached 1.0% by mass of the total mass of the zircon oxide particles (the content of an alkyl group in the zinc oxide particles coated with silicon oxide reached 0.08% by mass).

An aqueous composition containing the zircon oxide particles coated with silicon oxide of Example 2 was obtained in the same manner as in Example 1 except for the fact that the zircon oxide particles coated with silicon oxide of Example 2 were used instead of the zircon oxide particles coated with silicon oxide of Example 1.

Figure 4:
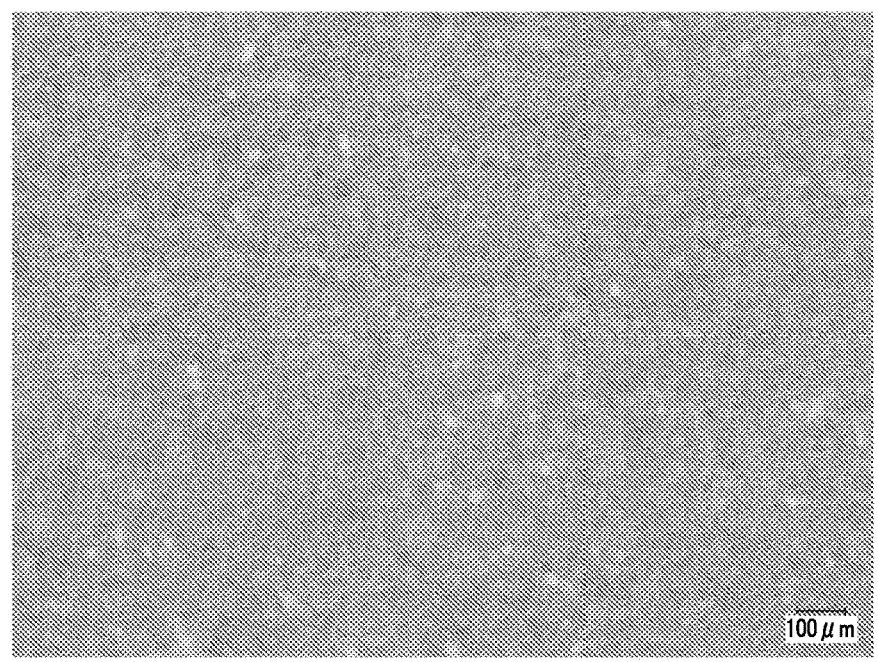
FIG. 4 is a view showing an optical microscopic image of the aqueous composition containing zircon oxide particles coated with silicon oxide of Example 2.

The dispersibility of the zircon oxide particles coated with silicon oxide in the aqueous composition was evaluated in the same manner as in Example 1. As a result, the maximum particle diameter in an observed agglomerate of the zinc oxide particles coated with silicon oxide was 30 μm. The result is shown in FIG. 4.

The surface wettability of the zircon oxide particles coated with silicon oxide was evaluated in the same manner as in Example 1.

As a result of visually observing the liquid mixture that had been left to stand for 20 hours, the liquid mixture was separated into a water phase and an oil phase, the water phase in which the zinc oxide particles coated with silicon oxide were dispersed became white-turbid, and the oil phase was transparent.

In addition, the spectral transmittance of the oil phase in the liquid mixture was measured in the same manner as in Example 1. As a result, it was confirmed that the transmittance at 360 nm was 100% and the surface state of the zinc oxide particle coated with silicon oxide of Example 2 was readily absorbed by water but not readily absorbed by oil.

The spectral transmittance of a thin film formed using the aqueous composition was measured in the same manner as in Example 1. The result is shown in FIG. 2. The SPF value was 6.9.

Figure 3:
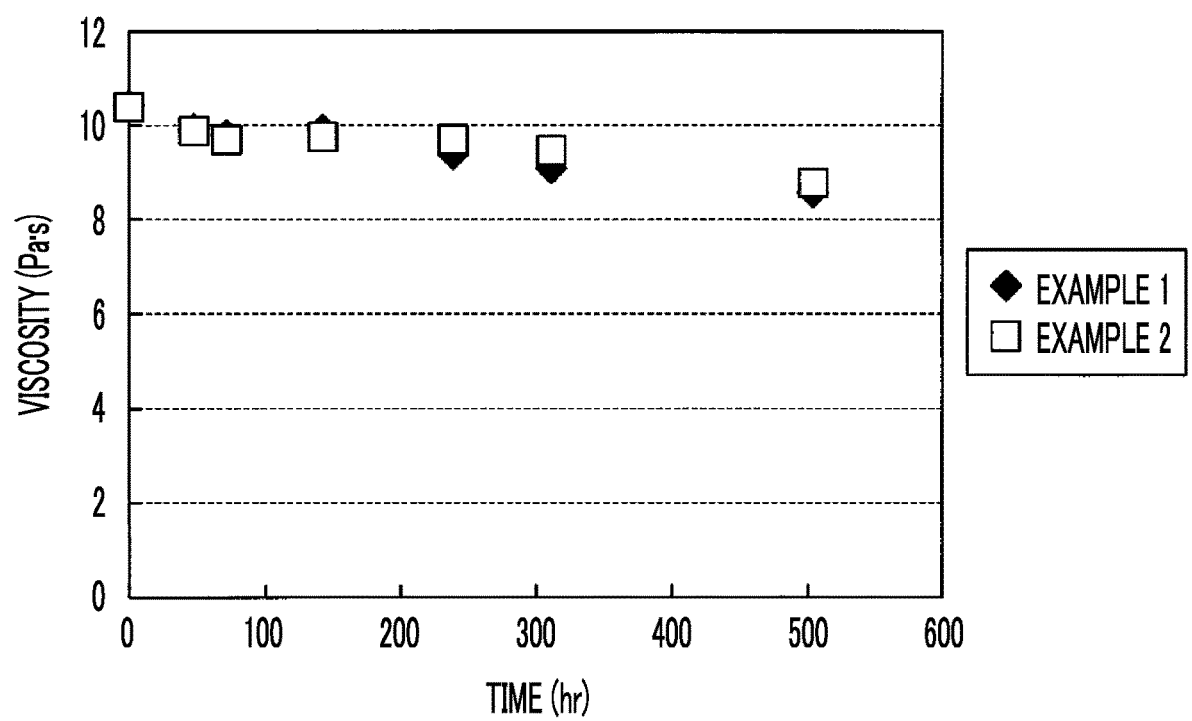
FIG. 3 is a view showing temporal changes of viscosities at 40° C. of the aqueous compositions containing zircon oxide particles coated with silicon oxide of Example 1 and Example 2.

The pH and the viscosity of the aqueous composition were measured in the same manner as in Example 1. The result is shown in FIG. 3 and Table 2.

Example 3

Zinc oxide particles coated with silicon oxide of Example 3 were obtained in the same manner as in Example 1 except for the fact that, in Example 1, the content of methyltriethoxysilane reached 3.0% by mass of the total mass of the zircon oxide particles (the content of an alkyl group in the zinc oxide particles coated with silicon oxide reached 0.25% by mass).

An aqueous composition containing the zircon oxide particles coated with silicon oxide of Example 3 was obtained in the same manner as in Example 1 except for the fact that the zircon oxide particles coated with silicon oxide of Example 3 were used instead of the zircon oxide particles coated with silicon oxide of Example 1.

Figure 5:
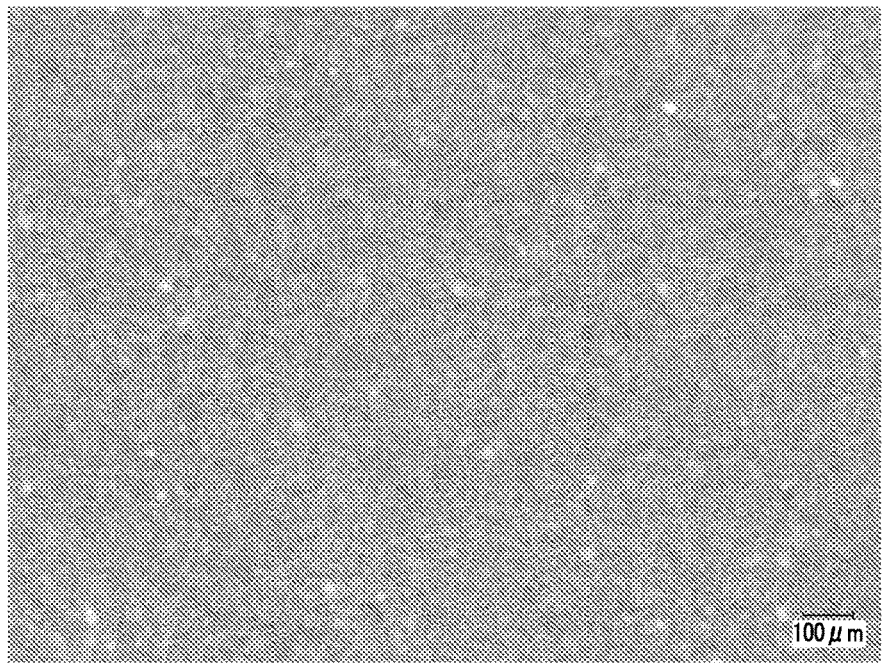
FIG. 5 is a view showing an optical microscopic image of the aqueous composition containing zircon oxide particles coated with silicon oxide of Example 3.

The dispersibility of the zircon oxide particles coated with silicon oxide in the aqueous composition was evaluated in the same manner as in Example 1. As a result, the maximum particle diameter in an observed agglomerate of the zinc oxide particles coated with silicon oxide was 30 μm. The result is shown in FIG. 5.

The surface wettability of the zircon oxide particles coated with silicon oxide was evaluated in the same manner as in Example 1.

As a result of visually observing the liquid mixture that had been left to stand for 20 hours, the liquid mixture was separated into a water phase and an oil phase, the water phase in which the zinc oxide particles coated with silicon oxide were dispersed became white-turbid, and the oil phase was transparent.

In addition, the spectral transmittance of the oil phase in the liquid mixture was measured in the same manner as in Example 1. As a result, it was confirmed that the transmittance at 360 nm was 99% and the surface state of the zinc oxide particle coated with silicon oxide of Example 3 was readily absorbed by water and also slightly absorbed by oil.

The spectral transmittance of a thin film formed using the aqueous composition was measured in the same manner as in Example 1. The result is shown in FIG. 2. The SPF value was 6.2.

Comparative Example 1

Zinc oxide particles coated with silicon oxide of Comparative Example 1 were obtained in the same manner as in Example 1 except for the fact that, in Example 1, the content of methyltriethoxysilane reached 0% by mass of the total mass of the zircon oxide particles (the content of an alkyl group in the zinc oxide particles coated with silicon oxide reached 0% by mass).

An aqueous composition containing the zircon oxide particles coated with silicon oxide of Example 1 was obtained in the same manner as in Example 1 except for the fact that the zircon oxide particles coated with silicon oxide of Comparative Example 1 were used instead of the zircon oxide particles coated with silicon oxide of Example 1.

Figure 6:
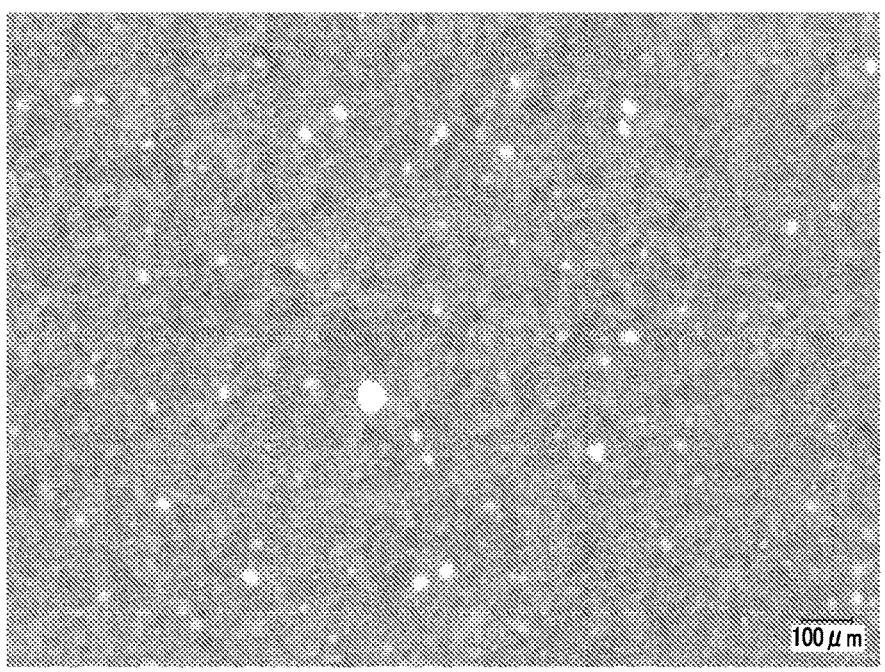
FIG. 6 is a view showing an optical microscopic image of the aqueous composition containing zircon oxide particles coated with silicon oxide of Comparative Example 1.

The dispersibility of the zircon oxide particles coated with silicon oxide in the aqueous composition was evaluated in the same manner as in Example 1. As a result, the maximum particle diameter in an observed agglomerate of the zinc oxide particles coated with silicon oxide was 80 μm. The result is shown in FIG. 6.

The surface wettability of the zircon oxide particles coated with silicon oxide was evaluated in the same manner as in Example 1.

As a result of visually observing the liquid mixture that had been left to stand for 20 hours, the liquid mixture was separated into a water phase and an oil phase, the water phase in which the zinc oxide particles coated with silicon oxide were dispersed became white-turbid, and the oil phase was transparent.

In addition, the spectral transmittance of the oil phase in the liquid mixture was measured in the same manner as in Example 1. As a result, it was confirmed that the transmittance at 360 nm was 100% and the surface state of the zinc oxide particle coated with silicon oxide of Comparative Example 1 was readily absorbed by water but not readily absorbed by oil.

The spectral transmittance of a thin film formed using the aqueous composition was measured in the same manner as in Example 1. The result is shown in FIG. 2. The SPF value was 3.3.

TABLE 1

|  | Example 1 | Example 2 | Example 3 | Comparative Example 1 |
|---|---|---|---|---|
| Content of methyl group (% by mass) | 0.04 | 0.08 | 0.25 | 0 |
| Maximum particle diameter (μm) of agglomerate | 20 | 30 | 30 | 80 |
| SPF value | 8.2 | 6.9 | 6.2 | 3.3 |

TABLE 2

| Time | Example 1 | | Example 2 | |
|---|---|---|---|---|
| (hr) | pH | Viscosity (Pa · s) | pH | Viscosity (Pa · s) |
| 0 | 8.6 | 10.4 | 8.7 | 10.4 |
| 48 | 8.8 | 9.9 | 8.8 | 9.9 |
| 72 | 8.7 | 9.8 | 8.7 | 9.7 |
| 144 | 8.8 | 9.9 | 8.8 | 9.8 |
| 240 | 8.7 | 9.4 | 8.7 | 9.7 |
| 312 | 8.7 | 9.1 | 8.7 | 9.5 |
| 504 | 8.7 | 8.6 | 8.7 | 8.8 |

When Example 1 to Example 3 and Comparative Example 1 are compared with each other, it is confirmed that, when at least one functional group selected from the group consisting of an alkyl group, an alkenyl group, and a cycloalkyl group is caused to be present on the surface of the silicon oxide coat, the agglomeration of the zinc oxide particles coated with silicon oxide at the time of being mixed with the carboxy vinyl polymer gel having a pH of 7.5 that is broadly used in aqueous cosmetics is suppressed, and the SPF value improves in the case of forming a coated film.

In addition, when Example 1 and Example 2 and Example 3 and Comparative Example 1 are compared with each other, it is confirmed that, when a state in which the surfaces of the zinc oxide particles coated with silicon oxide do not absorb decamethylcyclopentasiloxane and agglomeration is suppressed at the time of mixing the zinc oxide particles coated with silicon oxide and the carboxy vinyl polymer is formed, the SPF value improves in the case of forming a coated film.

In addition, it was confirmed that, even in the case of being applied to oil-in-water cosmetics, the agglomeration of the zinc oxide particles coated with silicon oxide is suppressed, and the SPF value is also high in the case of forming a coated film. The oil-in-water cosmetic is evaluated by being mixing with the synthetic sebum or being applied onto the synthetic sebum, the status is close to the actual use status. That is, it was confirmed that there is an extremely high possibility that the effect can be obtained even when the oil-in-water cosmetic is applied to human skin.

INDUSTRIAL APPLICABILITY

The ultraviolet-shielding particle coated with silicon oxide of the present invention is capable of obtaining a desired ultraviolet-shielding property even when contained in an aqueous cosmetic by causing a predetermined functional group to be present on at least a part of the surface of the ultraviolet-shielding particle coated with silicon oxide of the present. Therefore, the ultraviolet-shielding particle coated with silicon oxide can be applied to aqueous cosmetics or oil-in-water cosmetic products which demand an ultraviolet-shielding capability and have excellent sensation, furthermore, in the case of being used in non-cosmetic fields, broadens the range of choice of a dispersant or a resin, is capable of increasing the degree of freedom in designing and blending paint and the like, and has a significant industrial value.

The invention claimed is:

1. An ultraviolet-shielding particle coated with silicon oxide formed by coating a surface of the ultraviolet-shielding particle with a silicon oxide coat,
    wherein a content of silicon oxide in the silicon oxide coat is 10% by mass to 40% by mass based on a total amount of the ultraviolet-shielding particle coated with silicone oxide,
    wherein at least one functional group selected from the group consisting of an alkyl group, an alkenyl group, and a cycloalkyl group is present on a surface of the silicon oxide coat, and
    a content of the at least one functional group is 0.0001% by mass to 0.30% by mass or based on a total amount of the ultraviolet-shielding particle coated with silicon oxide.

2. The ultraviolet-shielding particle coated with silicon oxide according to claim 1, wherein a content of the ultraviolet-shielding particle is 50% by mass to 90% by mass.

3. An aqueous composition containing an ultraviolet-shielding particle coated with silicon oxide comprising:
    the ultraviolet-shielding particle coated with silicon oxide according to claim 1; and
    water.

4. A cosmetic comprising:
    ultraviolet-shielding particle coated with silicon oxide according to claim 1; and
    a cosmetic product base raw material.

5. An oil-in-water cosmetic comprising:
    ultraviolet-shielding particle coated with silicon oxide according to claim 1 in a water phase.

6. An aqueous composition containing an ultraviolet-shielding particle coated with silicon oxide comprising:
    ultraviolet-shielding particle coated with silicon oxide according to claim 2; and
    water.

7. A cosmetic comprising:
    ultraviolet-shielding particle coated with silicon oxide according to claim 2; and
    a cosmetic product base raw material.

8. A cosmetic comprising:
    the aqueous composition containing an ultraviolet-shielding particle coated with silicon oxide according to claim 3; and
    a cosmetic product base raw material.

9. An oil-in-water cosmetic comprising:
    ultraviolet-shielding particle coated with silicon oxide according to claim 2 in a water phase.

10. An oil-in-water cosmetic comprising:
    the aqueous composition containing an ultraviolet-shielding particle coated with silicon oxide according to claim 3 in a water phase.

* * * * *